United States Patent [19]
Svensson et al.

[11] Patent Number: 5,594,024
[45] Date of Patent: Jan. 14, 1997

[54] CENTRALLY ACTIG SUBSTITUTED PHENYLAZACYCLOALKANES

[75] Inventors: Kjell A. I. Svensson, Goteborg, Sweden; Hakan V. Wikstrom, Groningen, Netherlands; Per A. E. Carlsson, Goteborg, Sweden; Anna M. P. Boije, Lerum, Sweden; R. Nicholas Waters; Clas A. Sonesson, both of Goteborg, Sweden; Nils P. Stjernlof, Vastra Frolunda, Sweden; Bengt R. Andersson; Lars O. Hansson, both of Goteborg, Sweden

[73] Assignee: The Upjohn Company, Kalamazoo, Mich.

[21] Appl. No.: 455,474

[22] Filed: May 31, 1995

Related U.S. Application Data

[60] Division of Ser. No. 133,606, filed as PCT/US92/02227 Mar. 26, 1992, Pat. No. 5,462,947, which is a continuation-in-part of Ser. No. 686,799, Apr. 17, 1991, abandoned.

[51] Int. Cl.[6] .................... A61K 31/40; C07D 207/04
[52] U.S. Cl. .................... 514/429; 514/422; 546/218; 548/146; 548/215; 548/250; 548/517; 548/518; 548/577
[58] Field of Search .................... 548/577, 146, 548/517, 215, 518, 250; 546/218; 514/422, 429, 343

[56] References Cited

U.S. PATENT DOCUMENTS

| | | | |
|---|---|---|---|
| 4,188,396 | 2/1980 | Haas et al. | 514/317 |
| 4,259,337 | 3/1981 | Nedelec et al. | 514/317 |
| 4,263,438 | 4/1981 | Althuis et al. | 546/216 |
| 5,128,362 | 7/1992 | DeBernardis | 514/408 |
| 5,130,432 | 7/1992 | Cooper | 546/114 |
| 5,223,530 | 6/1993 | Parish | 514/423 |

FOREIGN PATENT DOCUMENTS

| | | | |
|---|---|---|---|
| 0244739 | 11/1987 | European Pat. Off. | C07D 207/06 |
| 0307121 | 3/1989 | European Pat. Off. | C07D 211/28 |
| 0309913 | 4/1989 | European Pat. Off. | C07D 207/06 |
| 0309914 | 4/1989 | European Pat. Off. | C07D 207/06 |
| 0372776 | 6/1990 | European Pat. Off. | C07D 471/04 |
| 0381235 | 8/1990 | European Pat. Off. | C07D 207/08 |
| 0435387 | 7/1991 | European Pat. Off. | C07D 409/06 |

OTHER PUBLICATIONS

K. Bogeso, et al., "Indolizidine and Quinolizidine Derivatives of the Dopamine Autoreceptor Agonist 3–(3–Hydroxyphenyl)–N–n–Propylpiperidine (3–PPP)", J. Med. Chem., 30, pp. 142–150 (1987).

H. Wikstrom, et al., "Resolved 3–(3–Hydroxyphenyl)–N–n Propylpiperidine and Its Analogues: Central Dopamine Receptor Activity", J. Med. Chem., 27, pp. 1030–1036 (1984).

G. Bianchi, et al., "Farmacologia della 3–fenilazetidina e di alcuni suoi derivati", IL Farmaco, Ed. Sci., vol. 21, No. 2, pp. 131–154 (1966).

H. Wikstrom, et al., "N–Substituted 1,2,3,4,4a,5,6,10b–Octahydrobenzo[f]quinolines and 3–Phenylpiperidines: Effects on Central Dopamine and o Receptors", J. Med. Chem., 30, pp. 2169–2174 (1987).

Haas, et al., Heterocyctes, Chem. Abst. 46433s, vol. 93 (1980).

(List continued on next page.)

Primary Examiner—Ceila Chang
Attorney, Agent, or Firm—Donald L. Corneglio

[57] ABSTRACT

A compound or Formula I

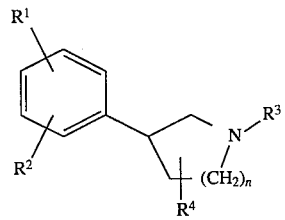

or a pharmaceutically acceptable salt thereof wherein n is 1 or 2; $R^1$ and $R^2$ are independently H (provided only one is H at the same time), —OH, CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, COR, COOR, $CON(R)_2$, $SO_xCH_3$ (where, x is 0–2), $SO_xCF_3$, $O(CH_2)_xCF_3$, $SO_2N(R)_2$, CH=NOR, COCOOR, COCOON$(R)_2$, $C_{1-8}$ alkyls, $C_{3-8}$ cycloalkyls, $CH_2OR$, $CH_2(R)_2$, $NRSO_2CF_3$, $NO_2$, halogen, a phenyl at positions 2, 3 or 4, thienyl, furyl, pyrrole, oxazole, thiazole, N-pyrroline, triazole, tetrazole or pyridine; $R^3$ is hydrogen, $CF_3$, $CH_2CF_3$, $C_1$–$C_8$ alkyl, $C_3$–$C_8$ cycloalkyl, $C_4$–$C_9$ cycloalkylmethyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkylene bonded to said nitrogen and one of its adjacent carbon atoms inclusive whereby a heterocyclic structure is formed; $R^4$ and R are independently selected from hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8; $R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$; $R^6$ and $R^7$ are independently hydrogen, $C_1$–$C_8$ alkyl, $C_3$–$C_8$ cycloalkyl, $C_4$–$C_9$ cycloalkylmethyl, $C_2$–$C_8$ alkenyl or $C_2$–$C_8$ alkynyl; and with the proviso that when $R^1$ is CN, $R^2$ and $R^4$ are H, $R^3$ is n-Pr and n is 1, then such compound is a pure enantiomer, and when $R^1$ or $R^2$ is OH, halogen, $CONH_2$ or alkyl, then $R^4$ is not hydrogen. The Formula I compounds possess selective pharmacological properties and are useful in treating central nervous system disorders related to dopamine receptor activity including depression symptoms, geriatric disorders in the improvement of mental and motor functions, schizophrenia, narcolepsy, MBD, obesitas, and disturbances of sexual functions and impotence.

9 Claims, No Drawings

OTHER PUBLICATIONS

D. Clark, et al., "Review Article: Dopamine–Receptor Agonists: Mechanisms Underlying Autoreceptor Selectivity", J. Neural Transmission, 62, pp. 1–52 (1985).

D. Clark, et al., "Review Article: Dopamine–Receptor Agonists: Mechanisms Underlying Autoreceptor Selectivity", J. Neural Transmission, 62, pp. 171–207 (1985).

U. Hacksell, et al., "3–Phenylpiperdines. Central Dopamine–Autoreceptor Stimulating Activity", J. Med. Chem., 24, pp. 1475–1482 (1981).

Hackwell et al "3–Phenylpiperidines. Central Dopamine autoreceptor stimulating activity" J. Med. Chem. v.24, 1475–1482 (1981).

CENTRALLY ACTIG SUBSTITUTED PHENYLAZACYCLOALKANES

CROSS-REFERENCE TO RELATED APPLICATIONS

This application is a divisional of U.S. Ser. No. 08/133,606, filed Oct. 12, 1993, now U.S. Pat. No. 5,462,947, which was a continuation of International PCT application PCT/US92/02227, filed Mar. 26, 1992, which was a continuation-in-part of U.S. Ser. No. 07/686,799, filed 17 Apr. 1991, abandoned.

FIELD OF THE INVENTION

The present invention is directed to new substituted 3-phenylpiperidine, 3-phenylpyrrolidine or 3-phenylazacycloheptenyl analogs, processes for preparing such compounds, pharmaceutical preparations of such compounds and the use of such compounds in the manufacture of a pharmaceutical preparation having dopamine receptor activity.

BACKGROUND OF THE INVENTION

In recent years a large body of pharmacological, biochemical and electrophysiological evidence has provided considerable support in favor of the existence of a specific population of central autoregulatory dopamine (DA receptors) located in the dopaminergic neuron itself and belonging to the D2 receptor subclass of DA receptors. These receptors are part of a homeostatic mechanism that modulates nerve impulse flow and transmitter synthesis and regulates the amount of DA released from the nerve endings. Recently, Sokoloff, et al., Nature, 347 146–51 (1990) presented evidence for the existence of a new type of dopamine receptor called D3. In a series of screened classical and atypical neuroleptics, the preferential dopamine autoreceptor antagonists (+)-A J76 and (+)-UH232 possessed the highest preference for the D3 site. The D3 receptor appears to occur both pre- and postsynaptically, and the regional distribution (high preference in limbic brain areas) differs from that of the D1 and D2 receptors.

Drugs acting as agonists or antagonists on central DA transmission are clinically effective in treating a variety of central nervous system disorders such as parkinsonism and schizophrenia. In parkinsonism, for example, the nigro-neostriatal hypofunction can be restored by an increase in postsynaptic DA receptor stimulation. In schizophrenia, the condition can be normalized by achieving a decrease in postsynaptic DA receptor stimulation. Classical antipsychotic agents directly block the postsynaptic DA receptor. The same effect can be achieved by inhibition of intraneuronal presynaptic events essential for the maintenance of adequate neurotransmission, transport mechanism and transmitter synthesis.

Direct DA receptor agonists, like apomorphine, are able to activate the DA autoreceptors as well as the postsynaptic DA receptors. The effects of autoreceptor stimulation appear to predominate when apomorphine is administered at low doses, whereas at higher doses the attenuation of DA transmission is outweighed by the enhancement of postsynaptic receptor stimulation. The antipsychotic and antidyskinetic effects in man of low doses of apomorphine are likely due to the autoreceptor-stimulator properties of this DA receptor agonist. This body of knowledge indicates DA receptor stimulants with a high selectivity for central nervous DA autoreceptors would be valuable in treating psychiatric disorders.

Compounds displaying preferential antagonistic effects at DA autoreceptors have been developed, Johansson et al., J. Med. Chem., 28, 1049 (1985). Examples of such compounds are (+)-cis-1S,2R-5-methoxy-1-methyl-2-(N-n-propylamino)tetralin ((+)-1S,2R-A J76) and (+)-cis-1S,2R-5-methoxy-1-methyl-2-(N,N-di-n-propylamino)tetralin ((+)-1S,2R-UH232). Biochemically these compounds behave as classical DA antagonists, e.g. like haloperidol. Consequently, they raise the Dopa accumulation in normal animals after the blockage of aromatic amino acid decarboxylase by NSD1015 and they raise the levels of the DA metabolites DOPAC and HVA (no NSD1015 treatment). However, functionally, in behavioral testing (photocell motility meters), they display stimulatory properties, e.g. they increase the locomotor activity. In addition, gross behavioral observations show that these compounds, in certain dosages, can induce a weak classical dopaminergic stereotypic behavioral effects like sniffing and rearing in rodents.

Diseases in which an increase in dopaminergic turnover may be beneficial are geriatrics, for preventing bradykinesia and depression and in the improvement of mental functions. It can have an effect in depressed patients. It can be used in obesitas as an anorectic agent. It can improve minimal brain dysfunction (MBD), narcolepsy and negative symptoms of schizophrenia. Improvement of sexual functions is another indication. Some of the compounds in this invention have both pre- and postsynaptic antagonistic effects. Compounds possessing more of the postsynaptic effects can be used to alleviate the symptoms (both positive and negative) of schizophrenia and for the rehabilitation of drug addicts. Other disturbances of interest in this context is "jet lag", sleep disorders and early stages of Parkinsonism.

INFORMATION DISCLOSURE STATEMENT

A number of 3-phenylpiperidine derivatives are known and described, for example, Hacksell et al., J. Med. Chem., 24, 1475 (1981) and Wikström et al., J. Med. Chem., 27, 1030 (1984). The reported compounds are 3-substituted 3-phenylpiperidines, most of them being 3-OH substituted and displaying pre- and postsynaptic dopaminergic agonistic effects. Clark et al. have presented two thorough reviews on the model autoreceptoragonist (−)-S-3-(3-hydroxyphenyl-N-n-propyl)piperidine ((−)-S-3-PPP).

The racemic compound 3-(3-cyanophenyl-N-n-propyl)piperidine has been published by Hacksell et al., J. Med. Chem., 24, 1475 (1981). In that publication it was found to display no direct receptor agonistic effects in reserpinized rats.

Rousell-Uclaf in U.S. Pat. No. 4,259,337 describes new 3-(3-trifluorophenyl)piperidines such as 3-(3-trifluoromethyl-N-n-propyl)piperidine with effects upon DA receptors.

Bøgesø, K.; Jørn, A.; Lundmark, M.; Sundell, S.; J. Med. Chem. 1987, 30, 142–150 discloses indolizidine and quinolizidine derivatives of 3-(3-hydroxyphenyl)-N-n-propylpiperidine, whereas in the subject invention $R^1$ and $R^2$ can only be —OH provided $R^4$ is not hydrogen.

SUMMARY OF THE INVENTION

The present invention is directed toward 1, 2 or 3-substituted 3-S-(phenyl-N-alkyl) pyrrolidine and 3-S-(phenyl-N-alkyl)piperidine compounds of Formula I

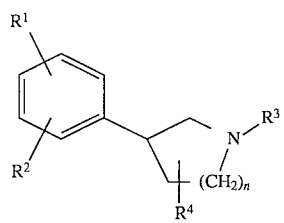

or a pharmaceutically acceptable salt thereof
wherein n is 1 or 2;

$R^1$ and $R^2$ are independently H (although only one can be H at the same time), —OH (provided $R^4$ is not hydrogen), CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, COR, COOR, $CON(R)_2$, $SO_xCH_3$ (where x is 0–2), $SO_xCF_3$, $O(CH_2)_xCF_3$, $SO_2N(R)_2$, CH—NOR, COCOOR, $COCOON(R)_2$, $C_{1-8}$ alkyls, $C_{3-8}$ cycloalkyls, $CH_2OR$, $CH_2(R)_2$, $NRSO_2CF_3$, $NO_2$, halogen phenyl (in positions 2, 3 or 4), thienyl, furyl, pyrrole, oxazole, thiazole, N-pyrroline, triazole, tetrazole or pyridine;

$R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkylene bonded to the N-atom and one of its adjacent carbon atoms whereby a heterocyclic structure is formed;

$R^4$ and R are independently selected from hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;

$R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$;

$R^6$ and $R^7$ are independently hydrogen, $C_1$–$C_8$ alkyl, $C_3$–$C_8$ cycloalkyl, $C_4$–$C_9$ cycloalkylmethyl, $C_2$–$C_8$ alkenyl or $C_2$–$C_8$ alkynyl; and with the provisos that when $R^1$ is CN, $R^2$ and $R^4$ are H, $R^3$ is n-Pr and n is 1, then such compound is a pure enantiomer (R or S) and not a racemic mixture; and when $R^1$ or $R^2$ is OH, halogen, $CONH_2$, or alkyl, then $R^4$ is not hydrogen.

The compounds of this invention possess selective dopamine receptor pharmacological properties and are useful in treating central nervous system disorders including depression symptoms, geriatric disorders in the improvement of mental and motor functions, schizophrenia, narcolepsy, MBD, obesity, disturbances of sexual functions and rehabilitation of drug abusers.

In one preferred embodiment, the invention is related to compounds of Formula I wherein $R^1$ is CN. In another preferred embodiment $R^1$ is CN and $R^2$ is n-Pr. The compounds of this invention relate to both racemic mixtures and the pure enantiomers (R or S). However, preferred compounds have the S absolute configuration, according to the Cahn-Ingold-Prelog priority rules. Depending on the N-substituent, some of these S-enantiomers are dextrorotatory while others are levorotatory.

In one aspect the invention is directed at providing compounds for dopamine receptor influenced therapeutic use, especially compounds having a therapeutic activity in the central nervous system of mammals including man. In yet another aspect this invention is directed at providing compounds having an effect on the subclasses of DA receptors known as the D2 and the D3 receptor.

DETAILED DESCRIPTION OF THE INVENTION

The compounds of this invention are identified in two ways: by the descriptive name and reference to labelled structures contained in the Formula Schemes (below). The compounds are identified by their stereochemistry (S, R or racemic) and a numeric designation as shown in Table 1, below, and in the other Tables and Schemes which follow. The preferred stereochemistry (S) is also represented in the charts.

TABLE 1

Table 1. D2 ([$^3$H]-spiperone) and 5-HT1A ([$^3$H]-8-OH-DPAT) in vitro binding data

| Compound | $R_1$ | $R_2$ | n | Formula | in vitro binding (IC50 nM) $D_2$-spip[a] | 5HT1A[b] |
|---|---|---|---|---|---|---|
| S-i | 3-OMe | n-Pr | 2 | $C_{15}H_{23}NO.HCl$ | 21000 | 4500 |
| S-(+)-13 | 3-$OSO_2CF_3$ | Me | 2 | $C_{13}H_{16}F_3NO_3S$ × HCl | 71000 | 2800 |
| S-(–)-14 | 3-$OSO_2CF_3$ | Et | 2 | $C_{14}H_{18}F_3NO_3S$ × HCl | 7100 | 1300 |
| S-(–)-15 | 3-$OSO_2CF_3$ | n-Pr | 2 | $C_{15}H_{20}F_3NO_3S$ × HCl | 1600 | 2300 |
| S-(–)-16 | 3-$OSO_2CF_3$ | n-Bu | 2 | $C_{16}H_{22}F_3NO_3S$ × HCl | 1300 | 1300 |
| S-17 | 3-$OSO_2CF_3$ | allyl | 2 | $C_{15}H_{18}F_3NO_3S$ × HCl | 28000 | 4200 |
| S-18 | 3-$OSO_2CF_3$ | $(CH_2)_2Ph$ | 2 | $C_{20}H_{23}F_3NO_3S$ | 240 | 230 |

TABLE 1-continued

Table 1. D2 ([$^3$H]-spiperone) and 5-HT1A ([$^3$H]-8-OH-DPAT) in vitro binding data

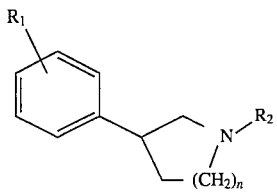

| Compound | R$_1$ | R$_2$ | n | Formula | in vitro binding (IC50 nM) D$_2$-spip[a] | 5HT1A[b] |
|---|---|---|---|---|---|---|
| Racemic-19 | 2-OSO$_2$CF$_3$ | n-Pr | 2 | C$_{15}$H$_{20}$F$_3$NO$_3$S × C$_2$H$_4$O$_4$ × HCl | 550 | 1400 |
| Racemic-20 | 4-OSO$_2$CF$_3$ | n-Pr | 2 | C$_{15}$H$_{20}$F$_3$NO$_3$S × HCl | 71000 | 14000 |
| Racemic-21 | 3-OSO$_2$CF$_3$ | n-Pr | 1 | C$_{14}$H$_{18}$F$_3$NO$_3$S × HCl | 4000 | 3200 |
| S-22 | 3-OSO$_2$CH$_3$ | n-Pr | 2 | C$_{15}$H$_{23}$NO$_3$S × HCl | 25000 | 1700 |
| S-25 | 3-COOCH$_3$ | n-Pr | 2 | C$_{16}$H$_{23}$NO$_2$ × HCl | 16000 | 2000 |
| S-(−)-29 | 3-CONH$_2$ | n-Pr | 2 | C$_{15}$H$_{22}$N$_2$O × HCl | 75000 | 6300 |
| S-31 | 3-CN | H | 2 | C$_{12}$H$_{14}$N$_2$ × HCl | 16000 | 10000 |
| S-(+)-32 | 3-CN | Me | 2 | C$_{13}$H$_{16}$N$_2$ × HCl | 50000 | 14000 |
| S-(−)-33 | 3-CN | Et | 2 | C$_{14}$H$_{18}$N$_2$ × HCl | 14000 | 22000 |
| S-(−)-34 | 3-CN | n-Pr | 2 | C$_{16}$H$_{20}$N$_2$ × HCl | 3500 | 75000 |
| R-(+)-34 | 3-CN | n-Pr | 2 | C$_{16}$H$_{20}$N$_2$ × HCl | 100000 | 14000 |
| S-35 | 3-CN | i-Pr | 2 | C$_{16}$H$_{20}$N$_2$ × HCl | 4300 | 16000 |
| S-36 | 3-CN | n-Bu | 2 | C$_{17}$H$_{22}$N$_2$ × C$_2$H$_4$O$_4$ | 3700 | 5600 |
| S-37 | 3-CN | allyl | 2 | C$_{16}$H$_{18}$N$_2$ × HCl | 8200 | 12000 |
| S-38 | 3-CN | cyclopropylmethyl | 2 | C$_{17}$H$_{20}$N$_2$ × HCl | 16000 | 7900 |
| S-39 | 3-CN | (CH$_2$)$_2$Ph | 2 | C$_{20}$H$_{22}$N$_2$ × C$_2$H$_4$O$_4$ | 630 | 150 |
| S-40 | 3-CN | (CH$_2$)$_2$Thiophen | 2 | C$_{18}$H$_{20}$N$_2$S × C$_2$H$_4$O$_4$ | 890 | 400 |
| S-41 | 3-CH=CH$_2$ | n-Pr | 2 | C$_{16}$H$_{23}$N × HCl | 3500 | 460 |

Footnotes Table 1.
[a]DA D2 ([$^3$H]-spiperone, antagonist binding) rat striatum.
[b]Serotonin 5-HT1A ([$^3$H]-8-OH-DPAT, agonist) rat cortex.

As used herein the term C$_{n-m}$ is inclusive such that a compound of C$_{1-8}$ would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl, n-pentyl, i-pentyl, neo-pentyl, n-hexyl, i-hexyl, n-heptyl, i-heptyl and n-octyl.

Alkenyl refers to a radical of an aliphatic unsaturated hydrocarbon having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl or 3-octenyl. Cycloalkyl refers to a radical of a saturated cyclic hydrocarbon such as cyclopropyl, cyclobutyl, cyclopentyl, cyclohexyl, cycloheptyl or cyclooctyl. Halogen refers to bromine, iodide, chlorine and preferably fluorine.

It will be apparent to those skilled in the art that compounds of this invention contain one chiral center. The compounds of Formula I contain an asymmetric carbon atom in the aliphatic ring moiety (carbon 3 in the heterocyclic ring to phenyl ring junction). The therapeutic properties of the compounds with DA autoreceptor blocking properties relate to compounds that have the S-stereochemistry. The scope of this invention includes both the S and the R enantiomers of the compounds of Formula I in their pure form. One R-enantiomer (R-3-(3-cyanophenyl-N-n-propyl)piperidine), (R)-34 was prepared and tested and was found to have essentially no affinity for D2 receptors (IC50=100000 nM in (3H)-Spiperone binding, as compared to IC50=3500 nM for S-3-(3-cyanophenyl-N-n-propyl)piperidine), but still, it stimulates the locomotor activity in habituated rats, obviously through another mechanism of action than the DA autoreceptor blockade seen with its S-analog (Tables 1 and 3). The (R)-34-enantiomer only weakly elevated limbic DOPAC (DA metabolism) levels and furthermore, it failed to produce locomotor stimulation or to affect the DA synthesis rate in reserpinized rats. This suggests that (R)-34 is devoid of direct agonistic or antagonistic actions at central dopamine receptors.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and outlined in Schemes 1–3.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated would be readily apparent to a person of ordinary skill in the art.

In therapeutical treatment an effective amount or a therapeutic amount of the compounds of the invention are from about 1 to about 2000 mg for oral application, preferentially 50–500 mg, and from about 0.1 to about 100 mg for parenteral application, preferentially 0.5–50 mg daily doses. The daily dose will preferably be administered in individual dosages one to 4 times daily and the dosage amounts are based on an individual having a weight of 70 kg.

The compounds of this invention where $R^1$ is cyano or O-triflate ($OSO_2CF_3$) and $R^3$ is $C_{1-8}$ alkyl are very selective DA receptor antagonists with a preferential action on DA autoreceptors. These compounds are particularly effective central stimulants possibly without self-administration liability. Uses for these compounds include geriatrics, for preventing akinesia and depression and the improvement of mental functions. They can have an effect in depressed patients. They can be used in obesitas as anorectic agents. They can improve minimal brain dysfunction (MBD) and narcolepsy. They can be useful in the rehabilitation of drug addicts. Some of the compounds in this invention have both pre- and postsynaptic antagonistic effects. Such compounds, with more of the postsynaptic effects, can be used to alleviate the symptoms (both positive and negative) of schizophrenia (see above).

The compounds of this invention also have been shown to have high oral potency and a long duration of action. Both these features are beneficial to effective clinical treatment.

The utility of the compounds of this invention to treat central nervous system disorders is shown in behavioral and biochemical activity in non-pretreated rats.

EXPERIMENTAL PROCEDURES

Locomotor Activity in Normal Non-Habituated and Habituated Animals

Non-habituated animals: The motor activity was measured (experiments were carried out between 9 a.m. and 1 p.m.) by means of photocell recordings (M/P 40 Fc Electronic Motility Meter, Motron Products, Stockholm) as described in Hacksell et al., J. Med. Chem., 22, 1469 (1979). The different test compounds were administered subcutaneously in the neck region or orally (in animals that had been starved over night) via a syringe equipped with a bent tube (n=4). Immediately after drug administration, the rats were placed in the test cages (one rat/cage) and put into the motility meters. Motor activity was then followed and recorded for the subsequent 30 minutes (Table 2). Observations of gross behavior were made throughout the activity sessions through semi-transparent mirrors.

TABLE 2

Table 2. Effects of some of the compounds of the present invention on DA and 5-HT synthesis rates and on motor activity in non-pretreated rats. Values are expressed as % of saline controls, mean ± sem.

| Compound (dose [mol/kg] | DOPA acc Stratium | DOPA acc Cortex | 5-HTP acc Limbic Region | Motor Act. | Gross Behavioral Observations |
|---|---|---|---|---|---|
| (−)-S-14 (100 sc) | 286 ± 33* | 80 ± 4 | 76 ± 9 | 103 ± 19 | No change |
| (−)-S-16 (100 sc) | 234 ± 10* | 89 ± 9 | 82 ± 5 | 116 ± 21 | No change |
| (+)-S-32 | | | | | |
| (25 sc) | 132 ± 9* | 91 ± 5 | 98 ± 7 | 128 ± 27 | No change |
| (100 sc) | 215 ± 6* | 109 ± 12 | 78 ± 2* | 79 ± 2* | Weak hypomot. Weak stimul. |
| (−)-S-33 | | | | | |
| (25 sc) | 282 ± 11* | 108 ± 7 | 83 ± 3 | 157 ± 7* | No change |
| (100 sc) | 318 ± 19* | 137 ± 7 | 77 ± 3* | 113 ± 7 | |
| (+)-34 | | | | | |
| (50 sc) | 281 ± 11* | 145 ± 11* | 82 ± 1 | 167 ± 19* | No change |
| (50 po) | 172 ± 8* | 103 ± 9 | 99 ± 3 | 133 ± 14 | No change |
| (−)-S-34 | | | | | |
| (50 sc) | 285 ± 3* | 155 ± 9* | 144 ± 6* | 154 ± 20* | Activation |

TABLE 2-continued

Table 2. Effects of some of the compounds of the present invention on DA and 5-HT synthesis rates and on motor activity in non-pretreated rats. Values are expressed as % of saline controls, mean ± sem.

| Compound (dose [mol/kg] | DOPA acc Stratium | Cortex | 5-HTP acc Limbic Region | Motor Act. | Gross Behavioral Observations |
|---|---|---|---|---|---|
| (100 sc) | 268 ± 16* | 158 ± 8* | 148 ± 10* | 165 ± 8* | Activation |
| (200 sc) | 294 ± 26* | 148 ± 16* | 80 ± 12 | 159 ± 24* | No change |
| (+)-R-34 | | | | | Weak |
| (50 sc) | 281 ± 11* | 145 ± 11* | 82 ± 1 | 167 ± 19* | stimulat. |
| (50 po) | 172 ± 8* | 103 ± 9 | 99 ± 3 | 133 ± 14 | No change |
| (−)-R-41 | 171 ± 15* | 121 ± 29 | 65 ± 2 | 125 ± 13 | No change |
| (100 sc) | | | | | |

\* Denotes statistically significant differences (p < 0.05, or less) compared to saline treated controls.
Footnotes Table 2. The animals were injected with test drugs and five min later put into photocell motility boxes, the activity (accumulated counts/30 min) was then measured and expressed as % of saline controls (230 ± 20 counts/30 min), mean ± sem, n = 4. Gross behavioral observations are commented to the right. After the session the rats were injected with NSD 1015 (100 mg/kg, i.p.) and then killed 30 min later. Shown is the DOPA accumulation in the DA rich striatal region, the DOPA accumulation in the NE-rich cortical regions and 5-HTP in the limbic forebrain.

TABLE 3

Table 3. Effects of some of the compounds of the present invention on DA and 5-HT metabolism in habituated rats. Values are expressed as % of saline treated controls, means ± SEM (n = 4).

| Compound (μmol/kg) | DOPAC striatum | DOPAC limbic | 5-HIAA limbic | Motor Activity | Behavioral observations |
|---|---|---|---|---|---|
| (+)-S-13 | 172 ± 11* | 138 ± 10 | 109 ± 2 | 135 ± 14 | No change |
| (100 sc) | | | | | |
| (−)-S-14 | 293 ± 29*** | 223 ± 39*** | 98 ± 33 | 404 ± 205* | Activation |
| (100 sc) | | | | | |
| (−)-S-15 | | | | | |
| (6.2 sc) | 118 ± 10 | 134 ± 10 | 139 ± 9 | 91 ± 94 | No change |
| (25 sc) | 175 ± 8* | 145 ± 11* | 126 ± 5 | 128 ± 33 | No change |
| (100 sc) | 217 ± 3* | 196 ± 16* | 140 ± 11 | 445 ± 131* | Activation |
| (−)-S-16 | 192 ± 4*** | 186 ± 2*** | 109 ± 4 | 345 ± 39** | Activation |
| (100 sc) | | | | | |
| S-17 | 222 ± 12*** | 159 ± 18** | 93 ± 6 | 195 ± 13* | Activation |
| (100 sc) | | | | | |
| S-18 | | | | 144 ± 23 | No activation |
| (25 sc) | | | | | |
| Racemic-19 | | | | 101 ± 14 | No activation |
| (100 sc) | | | | | |
| Racemic-21 | | | | 93 ± 18 | No activation |
| (100 sc) | | | | | |
| S-22 | 276 ± 12*** | 209 ± 11*** | 118 ± 11 | 550 ± 50** | Activation |
| (100 sc) | | | | | |
| S-31 | 167 ± 8*** | 153 ± 1%** | — | 431 ± 80* | Activation |
| (100 sc) | | | | | |
| (+)-S-32 | 120 ± 5 | 110 ± 6 | — | 277 ± 68* | Weak stim. |
| (100 sc) | | | | | |
| (−)-S-33 | 167 ± 8*** | 153 ± 15** | — | 431 ± 80* | Activation |
| (100 sc) | | | | | |
| (+)-S-34 | 291 ± 16* | 207 ± 6* | — | 878 ± 43* | Activation |
| (100 sc) | | | | | |
| (−)-S-34 | | | | | |
| (100 sc) | 362 ± 25* | 226 ± 11* | — | 653 ± 41* | Activation |
| (25 po) | 167 ± 10 | 138 ± 13 | — | 231 ± 31* | Activation |
| (400 po) | 259 ± 31 | 246 ± 10 | — | 338 ± 52* | Activation |
| (+)-R-34 | 117 ± 3 | 120 ± 5* | — | 650 ± 167* | Activation |
| (100 sc) | | | | | |
| S-35 | 251 ± 18*** | 335 ± 12*** | — | 336 ± 33* | Activation |
| (100 sc) | | | | | |
| S-37 | 298 ± 11 | 205 ± 17*** | — | 679 ± *** | Activation |
| (100 sc) | | | | | |
| S-38 | 272 ± 12*** | 221 ± 8*** | — | 518 ± 153** | Activation |
| (100 sc) | | | | | |

TABLE 3-continued

Table 3. Effects of some of the compounds of the present invention on DA and 5-HT metabolism in habituated rats. Values are expressed as % of saline treated controls, means ± SEM (n = 4).

| Compound (μmol/kg) | DOPAC striatum | DOPAC limbic | 5-HIAA limbic | Motor Activity | Behavioral observations |
|---|---|---|---|---|---|
| S-39 (100 sc) | 231 ± 14*** | 169 ± 16** | — | 511 ± 69** | Activation |
| S-40 (100 sc) | 201 ± 4*** | 149 ± 17* | — | 500 ± 92** | Activation |
| S-41 (100 sc) | 134 ± 13 | 136 ± 15 | 92 ± 14 | 529 ± 204* | Activation |

Footnotes Table 3. The rats were habituated to the motility meters 60 min prior to the activity session. Shown is the motor activity during a 60 min test session expressed as % of controls (94 counts/60 min), means ± SEM. The rats were immediately killed after the activity session, striatal and limbic levels of DOPAC and 5-HIAA were measured by means of HPLC-EC. *p < 0.05 or less compared to saline treated.

In-vivo determination of rat brain monoamine metabolites and tyrosine and tryptophan hydroxylation (biochemically monitored DA and 5-HT receptor agonist or antagonist activity).

The compounds under evaluation were tested biochemically for central DA and 5-HT receptor (pre- and/or postsynaptic) stimulating and/or blocking activity. The concept of this biochemical screening method is that a DA or 5-HT receptor agonist will stimulate the receptor and through regulatory negative feed-back systems induce a decline in tyrosine or tryptophan hydroxylating activity, respectively, and a subsequent reduction in the synthesis rate of DA and 5-HT in the presynaptic neuron. Dopa and 5-HTP formation, as determined after in-vivo inhibition of the aromatic L-amino acid decarboxylase with NSD 1015 (3-hydroxybenzylhydrazine hydrochloride) are taken as indirect measures of DA and 5-HT synthesis rates, respectively, as described by Wikström et al., J. Med. Chem., 27, 1030 (1984). The biochemical experiments and the determinations of Dopa and 5-HTP by means of HPLC with electrochemical detection were performed. The antagonistic effects were seen as increases in the synthesis rate (n=4), as a result of the positive feed-back upregulation of synthesis. The effects on Dopa and 5-HTP accumulation are expressed as % of controls, which were: DOPA limbic system=447±23 ng/g and DOPA striatum=1045±47 ng/g, 5-HTP limbic region 241±2 ng/g (Table 2).

In the experiments with habituated rats no NSD was administered and the animals were killed one hour after drug administration. The brains were dissected and the levels of DA, DOPAC (control levels: limbic 304±11 ng/g and striatum 843±24 ng/g), HVA (control levels: 175±9 ng/g and striatum 651±16 ng/g), 5-HT and 5-HIAA (control levels: limbic region: 388±45 ng/g) were measured by means of HPLC with electrochemical detection. The levels were expressed as % of controls (DOPAC and 5-HIAA see Table 3). The in vivo brain microdialysis experiments were performed in conscious rats as described by Waters et al., Eur. J. Pharm., 187, 425–34 (1990).

Animals used in the biochemical and motor activity experiments were male rats of the Sprague-Dawley strain (ALAB, Sollentuna, Sweden), weighing 200–300 g. The rats were kept 5 per cage with free access to water and food (except for the starved animals for the experiments with per oral administration, who were only allowed water the last 18 hours before testing), at least one week from arrival until used in the experiments.

All substances to be tested were dissolved in saline immediately before use, occasionally with the addition of a few drops of glacial acetic acid and/or moderate heating in order to obtain complete dissolution. Injection volumes were 5 mL/kg.

Analysis of variance (ANOVA) followed by Fischer's test was used for the statistical calculations. P values less than 0.05 were regarded statistically significant.

D2 antagonist binding. Preparation of rat striatal membranes for (3H)-spiperone (specific activity 21–24 Ci/mmol) binding was carried out in a similar manner as described for D1-binding, Hyttel et al., J. Neural. Transm., 68, 171 (1987). The final pellets were homogenized in 1300 volumes of 50 mM K-phosphate buffer and the membrane suspension was incubated with 0.5 nM (3H]-spiperone in a final volume of 4.2 mL (3 mg original tissue) for 10 minutes at 37° C. Specific binding was 70–80% of total binding and was obtained by adding 10 μM 6,7-ADTN to the membrane suspension.

5-HT1A radioligand binding. Male Sprague-Dawley rats (160–225 g) were killed by decapitation and the whole brain with the exception of the brainstem and cerebellum was rapidly removed, weighed and chilled in ice-cold 0.9% NaCl. Each brain was homogenized (Ultra-Turrax, 20 s) in 10 mL ice-cold 50 mM Tris buffer (pH 8.0 at 25° C.) containing 120 mM NaCl, 4 mM CaCl2 and 4 mM MgCl2 and centrifuged at 20,000 g's at 4° C. for 10 minutes. Pellets were resuspended in 10 mL fresh buffer and preincubated for 10 minutes in a 37° C. waterbath and then recentrifuged. Final pellets were homogenized in 100 volumes (w/v) of Tris buffer (as described above) containing 10 μM pargyline. The incubation tubes were kept on ice in triplicates and received 100 μL drug solution in water (or water for total binding) and 1000 μL membrane suspension (corresponds to 10 mg original tissue). The binding experiment was initiated by addition of 100 μL of (3H)-8-OH-DPAT (specific activity 143–158 Ci/mmol) in ascorbic acid (the final incubation concentration was 1 nM (3H)-8-OH-DPAT in 0.1% ascorbic acid). After incubation for 15 minutes at 37° C. the reaction was terminated by separation of the free radioligand from bound by rapid vacuum filtration using a cell harvester equipment (O. M. Teknik, Denmark). The tubes were rinsed with 4 mL and the filters (Whatman GF/F 25 mm) were washed twice with 4 mL ice-cold 0.9% NaCl.

The radioactivity of the filters was measured in a liquid scintillation counter (efficiency 41%) in 5 mL Picofluor®. Specific binding (70–75% of total binding) was defined as the radioactivity displaced by 10 μM 5-HT. IC50 values were calculated by semi-log plot and linear regression analysis.

The absence of significant decreases/increases in the DA metabolite levels in the hemispheral brain parts suggests that none of the compounds possess central NE receptor stimulating/blocking effects at the dosage under consideration.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Pharmacological Results

In vivo biochemical data, as exemplified with the prototypical test compounds S-(−)-34:

DOPA accumulation (DA synthesis rate) in non-pretreated rats (Table 2). After the locomotor activity session (see Table 2, above) the rats were injected with the decarboxylase inhibitor NSD 1015 (100 mg/kg, sc) and killed 30 minutes later. The DOPA accumulation in the DA -rich limbic and striatal and the NE-rich cortical (mainly hemispheres) brain areas were expressed as % of saline treated controls.

The DOPA accumulation was dose-dependently (3.1–200 μmol/kg, s.c.) elevated in the limbic (limb.) and striatal (stri) brain regions with a maximal response equal to that observed for classical neuroleptics such as haloperidol. The cortical (cort) DOPA formation was slightly, but statistically significantly increased. High doses (25 μmol/kg, sc and above) also weakly elevated (+45–50%) brain 5-HTP formation (Table 2). However, no statistical significant effects on brain 5-HIAA levels were observed (Table 3).

DOPA accumulation, time course after s.c. and p.o. administration (Table 2). The animals were injected with S-(−)-34 50 μmol/kg and killed after various time intervals (sc: 1.0, 2.5 and 4.5 hours; po 1.0 and 2.5 hours). NSD 1015 (100 mg/kg, sc) was injected 30 minutes before death. The data are expressed as % of saline treated controls.

The duration of the increase in brain DOPA accumulation was 2.5–4.5 hours after s.c. administration and 1.5–2.5 hours after po administration.

The effects on DOPA accumulation in the GBL-model is considered to reflect an event at the presynaptic dopamine autoreceptors (for further details, see Svensson et al., *Nunyn-Schmiedeberg's Arch. Pharm.*, 334, 234(1986)). GBL (750 mg/kg, i.p. 35 minutes before death) elevated the limbic and striatal DA synthesis rate. This effect was completely reversed by the dopamine agonist apomorphine (0.16 mg/kg, sc, 40 minutes before death).

S-(−)-34 (200 μmol/kg, sc, 40 minutes) blocked the effect of apomorphine but was inactive per se. A lower dose (100 μmol/kg, sc) of S-(−)-34 produced only a partial blockade of the apomorphine effect (data not shown). These data strongly indicate DA autoreceptor blocking effects of S-(−)-34 and no direct agonistic effects of the compound on central DA autoreceptors.

After the activity session the rats were killed and the brain levels of HVA and DOPAC were measured (data are expressed as means ±SEM). A pronounced and dose-dependent increase in brain DA metabolism was noted after sc administration of S-(−)-34. No effects on the brain levels of 5-HIAA were observed (Table 3).

The dialysis was performed in conscious rats implanted with a dialysis probe (Carnegie Medicin, Stockholm) in the caudate. S-(−)-34 (50 μmol/kg, sc) was injected when a stabile baseline was obtained. The perfusion media was a Ringer solution with a Ca2+ concentration of 1.2 mM. The perfusion rate was 2.0 μL/min and samples were collected every 20 minutes and analyzed on HPLC/EC. Effects on striatal DA release in the in vivo microdialysis model, time course are shown in Table 4. Data are expressed as % of controls, means ±SEM, n=4.

The increase in release of DA and in the levels of the DA metabolite DOPAC (Table 4) was similar to that noted for (+)-A J76 27 and classical DA receptor antagonists like haloperidol (unpublished data from this lab.). The duration of the effect was approximately 2.5 hours. The duration for the increase in DOPAC and HVA appears to be at least 4 hours. No consistent changes in the levels of 5-HIAA were noted (Table 4).

TABLE 4

Table 4. Microdialysis in rat striatum (% of control) for S-(−)-34 at 50 μmol/kg s.c., n = 4

| MINUTES | DA | HVA | DOPAC | 5-HIAA |
|---------|-----|-----|-------|--------|
| 0 | 100 | 100 | 100 | 100 |
| 20 | 180 | 140 | 180 | 110 |
| 40 | 240 | 200 | 250 | 115 |
| 60 | 280 | 250 | 295 | 120 |
| 80 | 300 | 280 | 300 | 115 |
| 100 | 280 | 300 | 295 | 115 |
| 120 | 275 | 310 | 280 | 110 |
| 140 | 225 | 300 | 260 | 105 |
| 160 | 200 | 305 | 250 | 110 |
| 180 | 190 | 280 | 230 | 110 |
| 200 | 180 | 220 | 215 | 110 |
| 220 | 160 | 230 | 190 | 100 |

In the in vitro binding assays (Table 1) S-(−)-34 had an IC50 of 3500 nM for the dopamine D2 receptor sites while the affinity for the 5-HT1A sites was much lower (IC50= 75000 nM).

In vivo behavioral data was obtained with rats injected with drug and 5 minutes later put into the motility chambers for the first time. The motor activity was measured for the subsequent 30 minutes (accumulated counts/30 minutes) and expressed as % of saline treated controls. S-(−)-34 produced a dose-dependent (25–200 μmol/kg, sc) monophasic increase in motor activity with a maximal effect of +60%.

Locomotor activity was measured in rats which were habituated 60 minutes to the activity meters before drug injection. The activity was measured for the subsequent 60 minutes and expressed as % of controls (means ±SEM, n=4). The activity of the habituated rats were approximately 10% of the activity of the non-habituated rats.

S-(−)-34 produced a strong locomotor stimulation (+600%) in the habituated rats. Stereotyped sniffing and rearing was also observed. The efficacy of S-(−)-34 is lower than that of d-amphetamine but similar or even somewhat higher than that of the preferential DA autoreceptor antagonists (+)-AJ76 and (+)-UH232 5.

It was shown that S-(−)-34-induced hypermotility in habituated rats is blocked by haloperidol, raclopride, reserpine and alpha-methyl-para tyrosine. The hypermotility induced by 50 μmol/kg s.c. of S-(−)-34 was blocked by the DA receptor blockers haloperidol and raclopride. The test compounds were administered consecutively at the same time. These results strongly suggests that the stimulation produced by S-(−)-34 was mediated via central dopamine receptors.

The catecholamine synthesis inhibitor alpha-methyl-para-tyrosine (Sigma, alpha-MT;100 mg/kg, i.p.) was administered 60 minutes before S-(−)-94 (50 mol/kg, s.c.). Alpha-MT alone did not affect the motor activity while it partially inhibited the locomotor stimulation produced by S-(−)-34. This suggests that the behavioral activation is indirectly mediated via an increase in the release of DA. The monoamine depleting agent reserpine (5 mg/kg, 18 h before) completely prevented the locomotor stimulation produced by S-(−)-34 (50 μmol/kg, sc). Also R-(+)-34 (50 μmol/kg, sc) failed to activate the reserpinized rats: 6±2 counts/30 min.

Effects on d-amphetamine-induced hyperactivity in habituated rats was measured where the rats were habituated to the motility meters for 60 minutes before injection of test drugs (d-amphetamine 0.5 or 5.0 mg/kg, sc; (+)-AJ76 14 mg/kg, sc and S-(−)-34 14 mg/kg, sc. The activity was measured for the subsequent 60 minutes and was expressed as accumulated counts/60 min (means ±SEM).

S-(−)-34, per se, produced a locomotor stimulation in habituated rats. S-(−)-34 failed to affect the strong activation induced by a high dose (5 mg/kg, sc) of d-amphetamine while (+)-AJ76 clearly blocked the stimulation produced by d-amphetamine. When combined with a lower dose of d-amphetamine (0.5 mg/kg, sc), S-(−)-34 produced an additive stimulatory effect. Also a higher dose (64 mg/kg, sc=200 pmol/kg) of S-(−)-34 failed to block the hyperactivity induced by d-amphetamine (5.0 mg/kg, sc) in habituated rats :d-amphetamine 871±68%; S-(−)-34+d-amphetamine: 773±158%; NaCl: 100±14% (% of NaCl controls), no statistical significant difference between d-amphetamine and d-amph. +S-(−)-34 was observed.

These results suggest that S-(−)-34 even at very high doses lacks detectable blocking properties at postsynaptic dopamine receptors. This is in contrast to the actions of the preferential dopamine autoreceptor antagonists (+)-AJ76 and (+)-UH232 5. The blood levels of (±)-34 were measured after oral (40 μmol/kg) and iv (5 μmol/kg) administration of the drug to male Sprague-Dawley rats (250–300 g) that were cannulated with catheters in the jugular vein and the arteria carotis. The levels of (±)-34 were measured in whole blood by means of GC-MS. A comparison of the areas under the curves yields an oral bioavailability of approximately 78%. The half-life was approximately 3 hours (i.v. curve). The oral availability is considerably better than the values obtained for (+)-UH232 and (+)-AJ76 (approximately 6 and 3%, respectively).

The biochemical actions of S-(−)-34 on indices of presynaptic dopaminergic autoreceptor activity indicate a profile indistinguishable from that of classical neuroleptics. S-(−)-34 stimulates DA synthesis rate (DOPA) accumulation and metabolism (DOPAC and HVA levels) in limbic and striatal brain regions. An increased release of DA is evident from the microdialysis study. These effects of S-(−)-34 is likely to be the result of a blockade of the presynaptic dopamine autoreceptors. This is also strengthened by the fact that S-(−)-34 blocks apomorphine in the GBL-model (considered to reflect activity at dopamine autoreceptors). In vitro, S-(−)-34 possesses, albeit weak, affinity to the dopamine D2 receptor site. Furthermore, as expected, the compound failed to affect the DOPA accumulation in reserpinized (5 mg/kg, 18 h) rats. This strongly indicates a lack of direct agonistic effects at central dopamine receptors.

In non-pretreated rats, S-(−)-34 elevated brain 5-HTP levels indicating an antagonistic affect also at central 5-HT1A receptors. However, it is likely that this response is of an indirect nature since S-(−)-34 failed to affect brain levels of 5-HIAA (both in habituated rats and in the microdialysis model) and also displayed a very low affinity for the 5-HT1A receptors in vitro. The slight increase in cortical DOPA accumulation suggest that S-(−)-34 might block central alpha 2-receptors.

In sharp contrast to classical neuroleptics, S-(−)-34 displayed stimulant effects on the locomotor activity in the behavioral assays. The degree of locomotor stimulation depend largely on the baseline activity of the rats. A pronounced activation with weak stereotypies (sniffing and rearing) was observed in habituated rats. The maximal degree of stimulation is lower than that observed after classical stimulants like d-amphetamine and apomorphine but higher than that produced by the preferential dopamine autoreceptor antagonists (+)-UH232 and (+)-AJ765.

The latter difference is most likely explained by the fact that S-(−)-34 appears to lack the ability to block postsynaptic DA receptors; S-(−)-34 failed to block d-amphetamine-induced hyperactivity even at high doses. Thus, S-(−)-34 appears to have an even higher preference for the dopamine autoreceptors than have (+)-UH232 and (+)-AJ76.

S-(−)-34 is likely to exert its effects via a selective blockade of the presynaptic dopamine autoreceptors. As a result of this the synthesis and release of dopamine is increased. The newly released dopamine will activate the postsynaptic DA receptors and produce a behavioral stimulation. The fact that the behavioral stimulation is blocked by raclopride and haloperidol strongly suggest that the effects of S-(−)-34 is mediated via central dopamine receptors. It is most likely that the DA autoreceptor blockade of S-(−)-34 results in an increased release of dopamine from the granular storage pool since the locomotor stimulation also is blocked by pretreatment with reserpine and alpha-MT.

The pharmacokinetic experiments show that S-(±)-34 clearly has a higher oral availability (78%) than both (+)-UH232 and (+)-AJ76 in the rat. It is very likely that similar favorable pharmacokinetic parameters is valid for the S-(−)-enantiomer. When comparing the effects on DOPA accumulation e.g. in the striatum (Table 2) after sc and po administration an estimated availability of 50% is obtained.

Taken together, the available pharmacological data strongly indicate that the prototype compound S-(−)-34 selectively blocks central dopamine autoreceptors and has favorable pharmacokinetic properties.

In the following examples, Examples 1–12, 50, 67, 73, and 76 are preparations for intermediates useful in preparing compounds of the invention which are depicted in Examples 13–49, 51–66, 68–72, 74, 75 and 77–82.

EXAMPLES

EXAMPLE 1

S-3-(3-Methoxyphenyl-N-n-propyl)piperidine (S-1)
(Scheme 2)

Preparation of the intermediate nitriles of the invention via O-Triflates

A solution of S-(−)-3-3-(hydroxyphenyl-N-n-propyl)piperidine (S-(−)-3-PPP) 7 (11 g, 50.2 mmol), triethyl-amine (0.151 g, 1.49 mmol), and solid sodium hydroxide (5 g, 129 mmol) in 100 ml THF was stirred at room temperature for 30 minutes. The temperature was increased to 30° C. and dimethyl sulphate (6.45 g, 51.2 mmol) is added over a period of about 2.5 hours maintaining the reaction temperature at 25°–30° C. by external cooling. The reaction mass is digested subsequently at about 60° C. for 2 hours. Most of the conversion takes place prior to digestion and digestion is intended also to destroy toxic dimethyl sulphate. Water (200 ml) was added, the mixture was stirred over night at room temperature, and was layered out. The aqueous phase was extracted with THF (3 portions) and the combined organic phase is washed with brine (2×50 ml), dried (MgSO$_4$) and evaporated and the conversions were determined quantitatively by GC. The residue after evaporation was used without any further purification. This product was characterized before Wikström, et al., in J. Med. Chem., 27 1030 (1984): m.p. 142°–145° C.

EXAMPLE 2

Intermediate S-3-(3-Methoxyphenyl)piperidine (S-2) (Scheme 2)

A solution of S-1 (7 g, 30 mmol) in 100 ml of ClCH$_2$CH$_2$Cl was cooled to 0° C. A α-chloroethyl chloroformate (6.45 g, 45.06 mmol) in 20 ml ClCH2CH2Cl was added dropwise at 0° C. The reaction mixture was refluxed for 5 hours. Two portions (1 ml ) of α-chloroethyl chloroformate were added during 48 hours. After this period the heating was interrupted and the volatiles were evaporated in vacuo. The residue was triturated with 100 ml MeOH and refluxed for 1.5 hours. The solvent was evaporated to afford S-2×HCl as light-brown crystals. The product was chromatographed on silica column with MeOH:CH$_2$Cl$_2$:NEt$_3$ (1:9:0.01) as eluant. Evaporation of the solvent afforded pure S-2×HCl, which was recrystallized from ethanol/isopropylether (4.1 g, 60%). This was characterized in Wikström et al., J. Med. Chem., 27 1030 (1984): m.p. 174°–176° C.

EXAMPLE 3

Intermediate S-3-(3-Methoxyphenyl-N-methyl)piperidine (S-3) (Scheme 2)

Compound S-3 was prepared from S-1 with the same method as described for S-4 (below) using paraform aldehyde instead of acetaldehyde. This was characterized in Wikström et al., J. Med. Chem., 27 1030 (1984).

EXAMPLE 4

Intermediate S-3-(3-Methoxyphenyl-N-ethyl)piperidine (S-4) (Scheme 2)

A mixture of S-2 (1.6 g, 8.38 mmol), NaCNBH$_3$ (2.11 g, 33.5 mmol), and acetaldehyde (1.47 g, 33.5 mmol), was dissolved in 25 ml of methanol. Glacial acetic acid (a few drops) was added until the pH of the suspension reached 4.5–5.0. The reaction mixture was stirred at room temperature for 20 hours at pH around 5.0 (adding more acid if necessary). The solvent was evaporated and to the residue was added 20 ml of water and 10 ml of conc. HCl The water solution was extracted with 3 portions of CH$_2$Cl$_2$, dried (MgSO$_4$), and evaporated to afford pure S-4 (2.0 g). The residue was used without any further purification. This product has been characterized in Wikström et al., J. Med. Chem., 27 1030 (1984).

EXAMPLE 5

Intermediate S-3-(3-Methoxyphenyl-N-n-butyl)piperidine (S-5) (Scheme 2)

Compound S-5 was prepared from S-2 as described above for S-4 using butyr-aldehyde instead of acetaldehyde. This product has been characterized in Wikström et al., J. Med. Chem., 27 1030 (1984).

EXAMPLE 6

Intermediate S-3-(3-Methoxyphenyl-N-allyl)piperidine (S-6) (Scheme 2)

To a suspension of S-2 (1.61 g, 8.42 mmol), grinded K$_2$CO$_3$(s) (0.66 g, 4.78 mmol) in 10 ml CH$_3$CN was allylic bromide (0.71 ml, 8.42 mmol) was added dropwise. The reaction mixture was stirred at room temperature for 2 hours when more K$_2$CO$_3$ (0.37, 2.68 mmol) was added. After 18 hours the reaction mixture was filtered, the solid was extracted with CH$_3$CN and the solvent was evaporated in vacuo. The residue was dissolved in CH$_2$Cl$_2$, washed with water, dried (Na$_2$SO$_4$), and evaporated (0.63 g). The pH of the waterphase was adjusted to 12 with NaOH and extracted 4 times with CH$_2$Cl$_2$ and drying (Na$_2$SO$_4$). The solvent was removed under reduced pressure and the residue (0.95 g) was used without any further purification, except for 150 mg, which was chromatographed on a silica column with CH$_2$Cl$_2$:MeOH (19:1) as eluent. Evaporation of the solvent, addition of ether to the remaining residue, and addition of etheral HCl to the ether solution afforded S-6×HCl (59%).

EXAMPLE 7

Intermediate S-3-)(3-Methoxyphenyl)-N-(2-phenylethyl))piperidine (S-7) (Scheme 2)

Compound S-7 was prepared from S-2 as described above for S-6 using 2-phenylethylbromide instead of allylbromide. This product has been characterized in Wikström et al., J. Med. Chem., 27 1030 (1984).

EXAMPLE 8

Intermediate S-3-(3-Hydroxyphenyl-N-methyl)piperidine (S-8) (Scheme 2)

A solution of S-3 (2.0 g) in fresh, aqueous 48% hydrogen bromide (25 ml) was stirred for 3 hours at 120° C. under argon atmosphere. The volatiles were evaporated in vacuo and the solid residue was partitioned between CH$_2$Cl$_2$ and a 10% Na$_2$CO$_3$-solution. The water phase was extracted with 2 portions of CH$_2$Cl$_2$. The combined organic phase was dried (MgSO$_4$), filtered and evaporated to afford pure S-8 (1.4 g). The residue was used without any further purification. This product has been characterized in Wikström et al., J. Med. Chem., 27 1030 (1984).

EXAMPLE 9

Intermediate
S-3-(3-Hydroxyphenyl-N-ethyl)piperidine (S-9)
(Scheme 2)

This product was prepared as described for compound S-8 above, and has been characterized in Wikström et al., J. Med. Chem., 27 1030 (1984).

EXAMPLE 10

Intermediate
S-3-(3-Hydroxyphenyl-N-n-butyl)piperidine (S-10)
(Scheme 2)

This product was prepared as described for compound S-8 above, and has been characterized in Wikström et al., J. Med. Chem., 27 1030 (1984).

EXAMPLE 11

Intermediate
S-3-(3-Hydroxyphenyl-N-allyl)piperidine (S-11)
(Scheme 2)

This product was prepared as described for compound S-8 above, and has been characterized in Wikström et al., J. Med. Chem., 27 1030 (1984).

EXAMPLE 12

Intermediate
S-3-((3-Hydroxyphenyl)-N-(2-phenylethyl))piperidine
(S-12) (Scheme 2)

This product was prepared as described for compound S-8 above, and has been characterized in Wikström et al., J. Med. Chem., 27 1030 (1984).

EXAMPLE 13

S-(+)-3-((3-(Trifluoromethyl)sulfonyl)oxyphenyl-N-methyl)-piperidine (S-(+)-13) (Scheme 1)

This product was prepared as described for compound S-15 below.

EXAMPLE 14

S-(−)-3-((3-(Trifluoromethyl)sulfonyl)oxyphenyl-N-ethyl)-piperidine (S-(−)-14) (Scheme 1)

This product was prepared as described for compound S-15 below.

EXAMPLE 15

S-(−)-3-((3-(Trifluoromethyl)sulfonyl)oxyphenyl-N-n-propyl)-piperidine (S-(−)-15) (Scheme 1) 24, 25

A solution of S-(−)-3-3(hydroxyphenyl-N-n-propyl)piperidine (S-(−)-3-PPP)6 (3.3 g, 15.07 mmol), 2,6-lutidine (2.42 g, 22.6 mmol) and 4-dimethyl-amino-pyridine (0.368 g, 3.01 mmol) in 300 ml $CH_2Cl_2$ was cooled to −30° C. Then the triflicanhydride (9.65 g, 34.2 mmol) in 30 ml $CH_2Cl_2$ was added dropwise. The reaction mixture was allowed to warm to room temperature and stirred for 2 hours at 25° C. The reaction was quenched with cold water. The layers were separated, and the organic phase was washed with 2 portions of cold 5% HCl-solution. Following a wash of the organic portion with brine and drying ($MgSO_4$). The solvent was removed under reduced pressure and the residue was used without any further purification, except for 200 mg, which was chromatographed on a silica column with $MeOH:CH_2Cl_2$ (1:19) as eluent. Evaporation of the solvent, addition of ether to the remaining solid, filtration of the insoluble $SiO_2$, and addition of etheral HCl to the ether solution afforded S-(−)-15×HCl: m.p. 156°–158° C.

EXAMPLE 16

R-3-((3-(Trifluoromethyl)sulfonyl)oxyphenyl-N-n-propyl)-piperidine (R-(+)-15) (Scheme 1)

This product was prepared as described for compound S-(−)-15 above.

EXAMPLE 17

S-(−)-3-((3-(Trifluoromethyl)sulfonyl)oxyphenyl-N-n-butyl)-piperidine (S-(−)-16) (Scheme 1)

This product was prepared as described for compound S-(−)-15 above.

EXAMPLE 18

S-3-((3-(Trifluoromethyl)sulfonyl)oxyphenyl-N-allyl)piperidine (S-17) (Scheme 1)

This product was prepared as described for compound S-(−)-15 above.

EXAMPLE 19

S-3-)(3-(Trifluoromethyl(sulphonyl)oxyphenyl))-N-(2-phenyl-ethyl))piperidine (S-18) (Scheme 1)

This product was prepared as described for compound S-(−)-15 above: m.p. 202°–205° C. (fumarate salt).

EXAMPLE 20

3-((2-(Trifluoromethyl)sulfonyl)oxyphenyl-N-n-propyl)piperidine (Racemic 19) (Scheme 1)

This product was prepared as described for compound S-(−)-15 above: m.p. 202°–204° C. (HCI salt).

EXAMPLE 21

3-((4-(Trifluoromethyl)sulfonyl)oxyphenyl-N-n-propyl)piperidine (Racemic 20) (Scheme 1)

This product was prepared as described for compound S-(−)-15 above.

EXAMPLE 22

3-((3-(Trifluoromethyl)sulfonyl)oxyphenyl-N-n-propyl)pyrrolidine (Racemic 21) (Scheme 1)

This product was prepared as described for compound S-(−)-15 above.

EXAMPLE 23

S-3-((3-Methylsulfonyl)oxyphenyl-N-n-propyl)piperidine (S-22)

A solution of S-(−)-3-3(hydroxyphenyl-N-n-propyl)piperidine (S-(−)-3-PPP)6 (200 mg, 0.91 mmol), triethylamine (101 mg, 1 mmol) in 15 ml $CH_2Cl_2$ was cooled to 0° C. Then the $CH_3SO_2Cl$ (136 mg, 1.19 mmol) in 5 ml $CH_2Cl_2$ was added dropwise. The reaction mixture was allowed to warm to room temperature and stirred for 2 hours at 25° C. The reaction was quenched with water, the layers were separated, and the organic phase was washed with 10% HCl and 10% $Na_2CO_3$. The organic phase was dried ($MgSO_4$) and the solvent was removed under reduced pressure. The residue was chromatographed on a silica column with $MeOH:CH_2Cl_2$ (1:12) as eluent. The solvents from the collected fractions containing pure S-22 were evaporated and addition of fumarate salt afforded S-22×fumarate (200 mg, 66%): m.p. 164°–165° C. (fumarate salt).

EXAMPLE 24

S-3-(3-(Methoxycarbonyl)phenyl-N-methyl)piperidine (S-23) (Scheme 1)

This product was prepared as described for compound S-25 below.

EXAMPLE 25

S-3-(3-(Methoxycarbonyl)phenyl-N-ethyl)piperidine (S-24) (Scheme 1)

This product was prepared as described for compound S-25 below.

EXAMPLE 26

S-3-(3-(Methoxycarbonyl)phenyl-N-n-propyl)piperidine (S-25) (Scheme 1) 24 26

A mixture of S-15 (5.5 g), triethylamine (3.17 g, 31.34 mmol), MeOH (20 g, 626.8 mmol), $Pd(OAc)_2$ (0.105 g, 0.47 mmol), 1.3 Bis.(diphenylphosphino)propane (0.194 g, 0.47 mmol) in 60 ml DMSO was stirred at room temperature for 15 minutes or until all particles were dissolved in the solution. A stream of CO was passed into the solution for 4–5 minutes, then the reaction vessel and contents were placed in a 70° C. oil bath under CO balloon. After 6 hours GC revealed complete absence of starting triflate S-15 and a 90% yield of the ester S-25. The reaction mixture was allowed to cold to room temperature. Water (200 ml) was then added. The water solution was extracted with 5 portions of $Et_2O$. The combined organic phases were washed with water until neutral, dried ($MgSO_4$) and evaporated. The residue was used without any further purification: m.p. 166°–167° C. (HCl salt).

EXAMPLE 27

R-3-(3-(Methoxycarbonyl)phenyl-N-n-propyl)piperidine (R-25) (Scheme 1)

This product was prepared as described for compound S-25 above.

EXAMPLE 28

S-3-(3-(Methoxycarbonyl)phenyl-N-n-butyl)piperidine (S-26) (Scheme 1)

This product was prepared as described for compound S-25 above.

EXAMPLE 29

S-3-(3-Carbamoylphenyl-N-methyl)piperidine (S-27) (Scheme 1)

This product was prepared as described for compound S-29 below.

EXAMPLE 30

S-3-(3-Carbamoylphenyl-N-ethyl)piperidine (S-28)

This product was prepared according to Scheme 1.

EXAMPLE 31

S-(−)-3-(3-Carbamoylphenyl-N-n-propyl)piperidine (S-(−)-29) (Scheme 1) 6

A suspension of S-25 (3.5 g, 13.4 mmol) in 10% NaOH solution (110 ml) and MeOH (30 ml) was refluxed until reaction was completed as shown by T.L.C (2.5 hours). The reaction mixture was acidified by 10% HCl and evaporated in vacuo. The solid residue was triturated with EtOH and filtered. Evaporation of the EtOH afforded the crude aminoacid hydrochloride as slight brown crystals.

The amino acid was heated in thionylchloride (10 ml) at 50° C. for 1.5 hours. After the addition of more thionylchloride (5 ml), the heating was continued for 1.5 hours. Evaporation of the excess thionylchloride gave an oil which crystallized on standing. The solid acylchloride that formed was dissolved in $CHCl_3$ (100 ml) and $NH_3$ (g) was slowly bubbled through the solution for 1 hour. The reaction mixture was evaporated, and the solid residue was triturated with $CH_2Cl_2$ (50 ml). The $NH_4Cl$ was filtered off, and the solvent was evaporated to afford S-(−)-29×HCl as light-brown crystals. This product was chromatographed on silica column with MeOH as eluent. Collection of the pure fractions of the product and evaporation of the solvent afforded pure S-(−)-29×HCl (2 g): m.p. 130° C.

EXAMPLE 32

R-3-(3-Carbamoylphenyl-N-n-propyl)piperidine (R-29) (Scheme 1)

This product was prepared as described for compound S-(−)-29 above.

EXAMPLE 33

S-3-(3-Carbamoylphenyl-N-n-butyl)piperidine (S-30)

This product was prepared according to Scheme 1.

EXAMPLE 34

S-3-(3-Cyanophenyl)piperidine (S-31) (Scheme 3)

A solution of S-(–)-34 (1.6 g, 7.02 mmol) in 30 ml of dichloroethane was cooled to 0° C. Then α-chloroethyl chloroformate (1.49 g, 10.5 mmol) in 10 ml dichloroethane was added dropwise at 0° C. The reaction mixture was refluxed for 10 hours. Three portions (1 ml) of α-chloroethyl chloroformate were added during three days. After this period the heating was interrupted and the volatiles were evaporated in vacuo. The residue was triturated with 75 ml MeOH and refluxed for 1.5 hours. The solvent was evaporated to afford S-31×HCl as light-brown crystals. The product was chromatographed on a silica column with MeOH as eluent. Evaporation of the solvent afforded pure S-31×HCl (1.0 g, 76%): m.p. 123°–124° C. (fumarate salt).

EXAMPLE 35

S-(+)-3-(3-Cyanophenyl-N-methyl)piperidine (S-(+)-32) (Scheme 1)

This product was prepared as described for compound S-(+)-34 below: m.p. 210°–212° C.

EXAMPLE 36

S-(–)-3-(3-Cyanophenyl-N-ethyl)piperidine (S-(–)-33) (Scheme 1)

This product was prepared as described for compounds-(–)-34 below: m.p. 192°–194° C.

EXAMPLE 37

S-(–)-3-(3-Cyanophenyl-N-n-propyl)piperidine (S-(–)-34) (Scheme 1)

A solution of S-(–)-29×HCl (1.42 g, 5.02 mmol), 1.8 ml POCl$_3$ in dry DMF (10 ml) was heated at 80° C. for 3 hours in argon-atmosphere. Evaporation of the reaction mixture gave a dark oily residue, which was dissolved in H$_2$O. The water solution was basified with saturated Na$_2$CO$_3$ solution and extracted several times with CH$_2$Cl$_2$. The combined organic layers were evaporated under reduced pressure and the residue was dissolved in Et$_2$O and insoluble particles were filtered off. The solvent was evaporated and the residue was chromatographed on a silica column with MeOH:CH$_2$Cl$_2$ (1:9) as eluant. Collection of the pure fractions and evaporation of the solvent, addition of Et$_2$O to the remaining solid, filtration of insoluble SiO$_2$, and addition of etheral HCl to the Et$_2$O solution afforded crystals of S-(–)-34×HCl. Recrystallization from ethanol/isopropylether gave pure crystals (1 g, 75%): m.p. 190°–191° C.

EXAMPLE 38

R-(+)-3-(3-Cyanophenyl-N-n-propyl)piperidine (R-(+)-34) (Scheme 1)

This product was prepared as described for compound S-(–)-34 above: m.p. 193°–194° C.

EXAMPLE 39

S-3-(3-Cyanophenyl-N-iso-propyl)piperidine (S-35) (Scheme 3)

This product was prepared as described for compound S-37 below: m.p. 185°–186° C.

EXAMPLE 40

S-3-(3-Cyanophenyl-N-n-butyl)piperidine (S-36) (Scheme 1)

This product was prepared as described for compound S-(–)-34 above: m.p. 117°–119° C.

EXAMPLE 41

S-3-(3-Cyanophenyl-N-allyl)piperidine (S-37) (Scheme 3)

A suspension of S-31 (173 mg, 0.778 mmol) and grinded K$_2$CO$_3$ (330 mg) was stirred in 10 ml of CH$_3$CN at room temperature. Allylbromide (97.5 mg, 0.806 mmol) dissolved in 1 ml of CH$_3$CN was added dropwise over a period of 2 hours. The mixture was stirred overnight. The reaction mixture was filtered, and the volatiles were evaporated in vacuo. The oily residue was chromatographed on a silica column with MeOH:CH$_2$Cl$_2$ (1:19) as eluent. Evaporation of the solvent afforded pure S-37. The amine was converted into the hydrochloride and recrystallized from ethanol/isopropylether (131 mg, 64%): m.p. 183°–185° C.

EXAMPLE 42

S-3-(3-Cyanophenyl-N-cyclopropylmethyl)piperidine (S-38) (Scheme 3)

This product was prepared as described for compound S-37 above.

EXAMPLE 43

S-3-((3-Cyanophenyl)-N-(2-phenylethyl))piperidine (S-39) (Scheme 3)

This product was prepared as described for compound S-34 above: The mixture was refluxed for 6 hours: m.p. 185°–187° C. (fumarate salt).

EXAMPLE 44

S-3-((3-Cyanophenyl)-N-(2-thiopheneethyl))piperidine (S-40) (Scheme 3)

This product was prepared as described for compound S-34 above: m.p. 195°–196° C. (fumarate salt).

EXAMPLE 45

S-3-(3-Vinylphenyl-N-n-propyl)piperidine (S-41)

To a solution of S-(–)-15 (837 mg, 2.39 mmol) in 10 ml of DMF were added tri-n-butylvinyl-stannane (787 mg, 2.48 mmol), LiCl (304 mg, 7.16 mmol), PdCl$_2$(PPh$_3$)$_2$ (33.5 mg, 0.047 mmol), and a few crystals of 2,6-di-tert-butyl-4-methylphenol. The resulting mixture was heated to 60° C. for 4 hours, cooled to room temperature, and treated with 1 ml of pyridine and 2 ml of pyridinium fluoride. The resulting mixture was stirred at 23° C. for 16 hours. The mixture was diluted with diethyl ether, filtered through a small pad of Celite, and washed with water, 10% HCl, water, and a concentrated sodium chloride solution. The solution was dried with $MgSO_4$ and concentrated to yield an oil. Chromatography (flash column, Methanol:$CH_2Cl_2$ 1:19) afforded S-41 as a colorless oil. The amine was converted into the hydrochloride and recrystallized from ethanol/isopropylether (200 mg, 32%).

EXAMPLE 46

S-(−)-3-(3-Ethynylphenyl)-N-n-propylpiperidine (S-(−)-42) (Scheme 4)

This compound was prepared as described for S-(−)-41 from S-(−)-15 (1.2 g, 3.41 mmol) and tri-n-butylethynylstannane (1.13 g, 3.58 mmol). Purification of the crude reaction mixture by flash chromatography ($CH_2Cl_2$/MeOH, 9/1 by volume) afforded 400 mg (52%) of pure S-42. The amine was converted into the hydrochloride salt and recrystallized from ethanol/isopropylether: m.p. 172°–74° C. (HCl); MS m/e 227.1 ($M^+$, 5.2), 199.1 (15.4), 198.1 (100), 128.05 (15.7), 15.05 (20.7), 70.05 (9.2);)$a)_D^{20}$ −9.7° C. (c=1.0, MeOH); Analysis calc'd for $C_{16}H_{22}NCl$: C, 72.85; H, 8.41; N, 5.31; found: C, 72.7; H, 8.5; N, 5.3.

EXAMPLE 47

S-(−)-3-(3-Methylphenyl)-N-n-propylpiperidine (S-(−)-43) (Scheme 4)

This compound was prepared as described for S-(−)-41 from S-(−)-15 (1.06 g, 3.02 mmol) and tetra-methylstannane (0.57 g, 3.18 mmol). Purification of the crude reaction mixture by flash chromatography (acetone/MeOH, 20/1 by volume) afforded 380 mg (58%) of pure S-43. The amine was converted into the hydro-chloride salt and recrystallized from ethanol/isopropylether: m.p. 193°–96° C. (HCl); MS m/e 217.15 (5.1, $M^+$), 189.15 (14.4), 188.15 (100), 145.05 (6.1), 118.05 (6.9), 105.05 (18.2), 86.05 (13.4), 70.05 (14.5); $a)_D^{20}$ −5.8° C. (c=1.0, MeOH); Analysis calc'd for $C_{15}H_{24}NCl$: C, 71.1; H, 9.55; N, 5.53; found: C, 71.0; H, 9.7; N, 5.55.

EXAMPLE 48

S-3-(3-(3-Thienyl)phenyl)-N-n-propylpiperidine (S-44) (Scheme 4)

This compound was prepared as described for S-(−)-41 from S-(−)-15 (1.22 g, 3.47 mmol) and tri-n-butyl-stannylthiophene (1.55 g, 4.16 mmol). Purification of the crude reaction mixture by flash chromatography ($CH_2C_2$/MeOH, 12/1 by volume) afforded 690 mg (70%) of pure S-44 as an oil: MS m/e 286.2 ($M^++1$, 1.5), 285.1 ($M^+$, 7.2), 257.1 (20.1), 256.1 (100), 186.00 (15.8), 173.0 (14.8), 128.0 (20.5).

EXAMPLE 49

S-(−)-3-(3-Acetylphenyl)-N-n-propylpiperidine S-(−)-45 (Scheme 4)

To a stirred solution of S-(−)-15 (1.87 g, 5.34 mmol) in DMF (18 mL) under an argon atmosphere at room temperature was sequentially added $Et_3N$ (1.63 g, 16 mmol), butylvinyl ether (4.01 g, 40 mmol), DPPP (309 mg, 0.749 mmol), and $Pd(OAc)_2$ (129 mg, 0.575 mmol). The reaction flask was heated to 80° C.C. After 0.5 h the conversion was complete (GLC) and the reaction mixture was cooled to room temperature, 5% HCl (30 mL) was added and after another 0.5 h of stirring the mixture was poured into $CH_2Cl_2$ (60 mL). The aqueous layer was extracted with $CH_2Cl_2$ (3×30 mL), and the combined organic layers were washed with water until neutrality, dried (anhydrous $MgSO_4$), filtered, and concentrated in vacuo. The crude product was purified by flash chromatography ($CH_2Cl_2$/MeOH, 9/1 by volume), affording S-(−)-45 (964 mg, 74%). The amine was converted into the hydro-chloride salt and recrystallized from ethanol/isopropylether: m.p. 151°–56° C. (HCl); MS m/e 245.15 ($M^+$, 3.3), 217.05 (15.8), 216.05 (100), 133.05 (5.0), 130.95 (5.6), 114.95 (4.8), 100.55 (6.1), 86.05 (6.2);$a)_D^{20}$ −5.1° C. (86.05 (6.2); $a)_D^{20}$ −5.1° C. (c=1.0, MeOH).

EXAMPLE 50

S-3-Phenyl-N-n-propylpiperidine (Intermediate) (S-46) (Scheme 4)

To a stirred solution of S-(−)-15 (500 mg, 1.42 mmol) in DMF (20 mL) under an argon atmosphere at room temperature were sequentially added $Et_3N$ (575 mg, 5.68 mmol), formic acid (261 mg, 5.68 mmol), $PPh_3$ (74.4 mg, 0.28 mmol), and $Pd(OAc)_2$ (47.8 mg, 0.21 mmol). The reaction temperature was raised to 60° C.C. After 6 h the reaction was complete (GLC) and the reaction mixture was cooled to room temperature, 5% HCl (30 mL) was added and after another 0.5 h of stirring the mixture was poured into $CH_2Cl_2$ (75 mL). The aqueous layer was extracted with $CH_2Cl_2$ (3×15 mL) and the combined organic layers were washed with water until neutrality, dried (anhydrous $MgSO_4$), filtered, and concentrated in vacuo. The crude product was purified by flash chromatography ($CH_2Cl_2$/MeOH, 9/1 by volume), affording 204 mg (71%) of pure S-46 as an oil: MS m/e 203.2 ($M^+$, 5.0), 175.1 (12.6), 174.1 (100), 104.04 (7.2), 91.05 (16.1), 70.05 (7.9).

EXAMPLE 51

1-3-(((Trifluoromethyl)sulfonyl)oxy)phenyl)quinolizidine (Racemic-47) (Scheme 1)

This compound was prepared as described for S-(−)-15 from 1-(3-hydroxyphenyl)quinolizidine (equatorial isomer)[28] (310 mg, 1.34 mmol) and triflic-anhydride (0.23 mL, 1.36 mmol). The crude product was purified by extractive work up, and afforded 390 mg (80%) of pure 47 as an oil: MS m/e calc'd for $F_3NO_3SC_{16}H_{20}$:363.112, found 363.114; 363.2 ($M^+$, 10.6), 230.25 (42.4), 125.15 (12.6), 111.15 (97.4), 98.15 (28.3), 97.15 (17.2), 96.15 (18.6), 83.15 (100).

EXAMPLE 52

S-8-3-(((Trifluoromethyl)sulfonyl)oxy)phenyl)indolizidine (S-48) (Scheme 1),

This compound was prepared as described for S-(−)-15 from S-8-(3-hydroxyphenyl)indolizidine[28] (140 mg, 0.55 mmol) and triflicanhydride (0.12 mL, 0.71 mmol). The crude product was purified by extractive work up, and afforded 190 mg (99%) of pure S-48 as an oil.: MS m/e $F_3NO_3SC_{15}H_{18}$: 349.104, found 349.096; 349.2 ($M^+$, 11.1), 216.25 (39.8), 147.15 (8.3), 97.15 (100), 96.15 (46.5), 91.15 (10.0), 84.15 (29.0), 83.15 (12.9).

EXAMPLE 53

3-3-(((Trifluoromethyl)sulfonyl)oxy)phenyl)-N-n-propylper-hydroazepine (Racemic-49) (Scheme 1)

This compound was prepared as described for S-(−)-15 from 3-(-3-hydroxy-phenyl)-N-n-propylperhydroazepine[6] (146 mg, 0.64 mmol) and triflic-anhydride (198 mg, 0.74 mmol). Purification of the crude reaction mixture by flash chromatography ($CH_2Cl_2$/MeOH, 19/1 by volume) afforded 195 mg (83%) of pure racemic-49 as an oil: MS (EI(70 eV)) m/e calc'd for $F_3NO_5SC_{16}H_{22}$: 365.127, found 365.119; 365.15 (3.3, $M^+$), 337.05 (18.9), 336.05 (40.6), 126.05 (38.1), 112.05 (23.9), 84.05 (100).

EXAMPLE 54

S-3-(2-bromo-5-((Trifluoromethyl)sulfonyl)oxyphenyl)-N-n-p ropyl-piperidine (S-50) (Scheme 1)

This compound was prepared as described for S-(−)-15 from S-61 (0.7 g, 2.36 mmol) and triflicanhydride (0.67 g, 2.36 mmol). Purification of the crude product by flash chromatography (petroleum ether/diethyl ether, 1/3 by volume) afforded 0.50 g (49%) of pure S-50 as an oil. The amine was converted to the hydrochloride salt with HCl-saturated ethanol, and recrystallized from ethanol/isopropylether: m.p. 178°–80° C. (HCl); MS m/e 429 ($M^+$, 3), 431 ($M^++2$, 4), 402 (100), 400 (93), 269 (66), 267 (50), 69 (28), 70 (35), 86 (30).

EXAMPLE 55

S-3-3-(((Trifluoromethyl)sulfonyl)amino)phenyl)-N-n-propy l-piperidine (S-51) (Scheme 1 )

This compound was prepared as described for S-(−)-15 from (intermediate, S-63) (230 mg, 1.05 mmol) and triflicanhydride (326 mg, 1.16 mmol). Purification of the crude product by flash chromatography ($CH_2Cl_2$/MeOH, 9/1 by volume) afforded 176 mg (48%) of pure S-51 as crystals: m.p. 124°–28° C. (base) MS m/e 350.2 ($M^+$, 2.6), 322.15 (16.2), 321.15 (100), 188.25 (12.3), 187.25 (20.0), 160.15 (9.2), 144.15 (10.0).

EXAMPLE 56

Cis-2-Methyl-4-(((3-trifluoromethyl)sulfonyl)oxy)-N-n-prop yl pyrrolidine. (Racemic-cis-52) (Scheme 5)

To a cold (−30° C. C) solution of cis-2-Methyl-4-(3-hydroxyphenyl)-N-n-propyl pyrrolidine (cis-77, 227 mg, 1.04 mmol) in dichloromethane (10 mL) was added triethylamine (0.23 mL, 1.66 mmol) followed by the dropwise addition of tri-fluoromethanesulfonic anhydride (0.25 mL, 1.48 mmol) dissolved in dichloro-methane (5 mL). After the addition the mixture was stirred at low temperature for 30 min. and then further for 30 min at ambient temperature. The reaction mixture was quenched by the addition of 15% sodium hydroxide (20 mL). The dichloro-methane layer was separated and extracted with 10% hydrochloric acid (2×20 mL). The acidic solution was washed with diethyl ether (2×10 mL), made alkaline by the addition of 50% sodium hydroxide (10 mL) and then extracted with diethyl ether (3×10 mL). Drying ($MgSO_4$) and removal of the solvent afforded 357 mg (98%) of the title compound as an oil: MS (EI) m/e calc'd for $C_{15}H_{20}F_3NSO_3$: 351.112, found 351.116; 351.10 (5, $M^+$), 336.10 (30), 323.10 (14), 322.10 (90), 217.20 (17), 203.10 (55), 189.10 (100), 147.10 (16), 117.00 (17), 115.00 (14), 91.00 (28), 84.10 (44), 77.00 (11).

EXAMPLE 57

S-(−)-3-(3-Cyanophenyl)-N-propargylpiperidine (S-(−)-53) (Scheme 3)

This compound was prepared as described for S-37 from S-(−)-31 (363 mg, 1.95 mmol) and propargylbromide (237 mg, 1.99 mmol). Purification of the crude reaction mixture by flash chromatography ($CH_2Cl_2$/MeOH, 25/1 by volume) afforded 302 mg (69%) of pure S-(−)-53 as an oil. The amine was converted to the hydrochloride salt with HCl-saturated ethanol and recrystallized from ethanol/isopropyl ether: m.p. 195°–96° C. (HCl); a)$_D^{20}$ −7.6° C. (c=1.0, MeOH); Analysis calc'd for $C_{15}H_{16}N_2 \times HCl$: C, 69.09; H, 6.57; N, 10.74; found: C, 69.0; H, 6.6; N, 10.5.

EXAMPLE 58

S-(−)-3-(3-Cyanophenyl)-N-3-phenylpropylpiperidine (S-(−)-54) (Scheme 3)

This compound was prepared as described for S-37 from S-(−)-31 (350 mg, 1.88 mmol) and 1-bromo-3-phenylpropane (237 mg, 1.99 mmol). Purification of the crude reaction mixture by flash chromatography ($CH_2Cl_2$/MeOH, 30/1 by volume) afforded 410 mg (72%) of pure S-(−)-54 as an oil. The amine was converted into the fumarate salt and recrystallized from ethanol/isopropyl ether: m.p. 158°–59° C. (fumarate); a)$_D^{20}$ −18.6° C. (c=1.0, MeOH); Analysis calc'd for $C_{21}H_{24}N_2 \times C_4H_4O_4$: C, 71.41; H, 6.71; N, 6.66; found: C, 71.33; H, 6.68; N, 6.62.

EXAMPLE 59

S-(−)-3-(3-Cyanophenyl)-N-3-(N,N dimethylaminopropyl)-piperidine (S-(−)-55 (Scheme 3)

This compound was prepared as described for S-37 from S-(−)-31 (416 mg, 2.24 mmol) and 3-dimethylaminopropyl chloride hydrochloride (371 mg, 2.35 mmol). Purification of the crude reaction mixture by flash chromatography ($CH_2C_2$/MeOH, 3/1 by volume) afforded 230 mg (38%) of pure S-(−)-55 as an oil. The amine was converted into the hydrochloride with HCl-saturated ethanol and recrystallized from methanol/isopropyl ether: m.p. 264°–66° C. (HCl); MS m/e 271.25 ($M^+$, 4.8), 226.15 (60.8), 211.15 (69.0), 199.15 (47.4), 197.15 (25.4), 110.05 (28.7), 86.05 (100);)a)$_D^{20}$ −21.6° C. (c=1.0, MeOH); Analysis calc'd for $C_{17}H_{21}N_3 \times 2$ HCl: C, 59.3; H, 7.9; N, 12.2; found: C, 58.7; H, 7.9; N, 12.0.

EXAMPLE 60

S-(−)-3-(3-Cyanophenyl)-N-2-butylpiperidine (S-(−)-56) (Scheme 3)

This compound was prepared as described for S-37 from S-(−)-31 (0.7 g, 3.76 mmol) and 2-iodobutane (0.7 g, 3.8 mmol). Purification of the crude reaction mixture by flash chromatography ($CH_2Cl_2$/MeOH, 19/1 by volume) afforded 700 mg (77%) of pure S-(−)-56 as an oil. The amine was converted into the fumarate salt, and recrystallized from ethanol/isopropyl ether: m.p. 153°–57° C. (fumarate); MS m/e 242.25 ($M^+$, 1.1), 227.25 (8.2), 214.25 (15.9), 213.25

(100), 142.2 (4.4), 129.1 (5.0), 116.1 (10.6);)a$_D^{20}$ −19.9° C. (c=1.0, McOH).

EXAMPLE 61

3-(3-Cyanophenyl)-N-n-propylpyrrolidine (Racemic-57) (Scheme 4)

Tetrakis(triphenylphosphine)palladium (7.2 g, 6.23 mmol) and tributyltin-cyanide (5.47 g, 17.3 mmol) in 60 mL of dichloroethane were heated under argon at 80° C.C for 2 h. To this refluxing solution was added in one portion racemic-21 (700 mg, 2.08 mmol) in 40 mL of dichloroethane. The reaction was heated at 80° C.C under argon for 24 h. The mixture was cooled to room temperature and the solid precipitate was filtered off. The mixture was concentrated in vacuo and the residue redissolved in 10% HCl (35 mL). The aqueous solution was extracted with diethylether (3×30 mL) to remove impurities. The resulting aqueous phase was basified with 15% NaOH and extracted with diethyl ether (4×20 mL). The combined organic phases were washed with brine, dried (MgSO$_4$), and evaporated in vacuo. The residue was purified by flash chromathography (CH$_2$Cl$_2$/MeOH, 12/1 by volume) afforded 214 mg (48%) of pure racemic-57 as an oil: MS m/e calc'd for N$_2$C$_{13}$H$_{18}$: 214.147, found 214.144; 214.1 (M$^+$, 3.9), 186.1 (13.7), 185.1 (100), 129.0 (10.4), 116.0 (13.8), 84.0 (23.7).

EXAMPLE 62

S-3-(2-Nitro-5-((trifluoromethyl)sulfonyl)oxyphenyl)-N-n-p ropyl-piperidine (S-58) (Scheme 4)

To an ice-cooled solution of S-(−)-15 (390 mg, 1.11 mmol) in nitromethane (15 mL) was slowly added dropwise a mixture of fuming nitric acid and conc. sulphuric acid (8 mL, 33:67 by volume). The mixture was allowed to reach ambient temperature and was stirred 0.5 h at room temperature. After pouring on ice water the mixture was basified with 10% sodium carbonate and extracted with diethylether (3×25 mL). The organic phase was dried (MgSO$_4$), filtered and evaporated to afford 440 mg (100%) of S-58. The oily residue was purified by flash chromatography on a silica column with (CH$_2$Cl$_2$/MeOH, 12/1 by volume) as eluent. Evaporation of the solvent afforded pure S-58 (240 mg, 74%) as an oil.: MS m/e 396.05 (M$^+$, 2.8), 367.95 (15.7), 366.95 (100), 233.95 (15.4), 192.00 (8.6), 188.00 (9.7), 146.00 (5.9).

EXAMPLE 63

S-3-(2-Nitrophenyl)-N-n-propylpiperidine (S-59) (Scheme 4)

This compound was prepared as described for S-58 from S-46 (140 mg, 0.689 mmol). Purification of the crude reaction mixture by flash chromatography (CH$_2$Cl$_2$/MeOH, 12/1 by volume) afforded 34 mg (20%) of pure S-59 as an oil MS m/e 247.95 (M$^+$, 2.0), 220.05 (12.6), 219.00 (100), 144.00 (11.6), 130.00 (13.6), 84.00 (33.2).

EXAMPLE 64

S-3-(4-Nitrophenyl)-N-n-propylpiperidine (S-60) (Scheme 4)

This compound was prepared as described for S-58 from S-46 (140 mg, 0.689 mmol). Purification of the crude reaction mixture by flash chromatography (CH$_2$Cl$_2$/MeOH, 12/1 by volume) afforded 105 mg (62%) of pure S-60 as an oil: MS m/e 248.2 (M$^+$, 2.8), 220.1 (13.7), 219.1 (100), 173.1 (5.0), 130.05 (11.1), 115.05 (5.7).

EXAMPLE 65

S-3-(2-bromo-5-hydroxyphenyl)-N-n-propylpiperidine (S-61) (Scheme 4)

To a solution of S-(−)-(3-hydroxy-phenyl)-N-n-propylpiperidine hydro-chloride[7] (1.4 g, 5.6 mmol) in CH$_2$Cl$_2$ (400 mL) was added slowly a solution of pyridinium-perbromide hydrobromide (4.04 g, 6.4 mmol) in CH$_2$Cl$_2$ (200 mL) at 0° C.C. When the addition was complete the temperature was raised to ambient temperature. The progress in reaction was monitored by GLC. When the reaction was complete the mixture was poured into 10% sodium carbonate and the resulting mixture was stirred for 0.5 h. The phases were separated and the organic phase was dried (MgSO$_4$), filtered and evaporated. The residue was re-dissolved in 99% ethanol and evaporated repetedly 3 times to a residue of 1.65 g (99%).: m.p. 103°–07° C. (HCl) MS m/e 297 (M$^+$, 7), 299 (M$^+$+2, 7), 268 (100), 270 (98), 70 (30), 86 (24), 146 (20).

EXAMPLE 66

S-(+)-3-(3-(2,2,2-Trifluoroethoxy)-phenyl)-N-n-propylpiperidine S-(+)-62)

A solution of S-(−)-3-PPP[7] (1.86 g, 8.49 mmol) in anhydrous DMF (50 mL) was added to sodium hydride (199 mg, 8.66 mmol) under nitrogen at room temperature. The mixture was stirred for 1 h at 40° C.C, followed by addition of the 2,2,2-tri-fluoroethyl p-toluenesulfonate (2.27 g, 8.91 mmol). The mixture was stirred at 80° C.C under nitrogen for 20 h. The reaction mixture was then cooled, poured into ice/water, and the aqueous solution was extracted with diethylether (4×30 mL). The combined etheral extracts were washed with a 5% aqueous NaOH and brine, dried (MgSO$_4$), and evaporated. The residue was purified by flash chromato-graphy (petroleum ether-ethyl acetate-Et$_3$N, 85:10:5, by volume), which afforded 790 mg (31%) of the title compound as a colorless oil. The amine was converted into the hydrochloride salt and recrystallized from ethanol/diethylether: m.p. 156°–60° C. (HCl); MS m/e 301.15 (M$^+$, 4.2), 273.05 (15.8), 272.15 (100), 189.05 (12.5), 86.10 (9.7), 70.20 (10.8);)a$_D^{20}$ −6.7° C. (c=1.0, MeOH); Analysis calc'd for C$_{16}$H$_{23}$F$_3$Cl: C, 56.89; H, 6.86; N, 4.15; found: C, 56.8; H, 6.9; N, 4.0.

EXAMPLE 67

S-3-(3-Aminophenyl)-N-n-propylpiperidine (Intermediate, S-63) (Scheme 4)

To a solution of S-25 (10 g, 38.31 mmol) in concentrated sulphuric acid (240 mL) and CH$_2$Cl$_2$ (400 mL) was added carefully NaN$_3$ (15 g, 231 mmol). After the addition was completed, the mixture was refluxed (50° C.C). Over a period of 6 h small portions of NaN$_3$ (3×2 g) were added to the reaction mixture. After refluxing for 20 h, the reaction was cooled to room temperature and quenched with ice water. The aqueous solution was basified with 50% NaOH and the layers were separated. The aqueous phase was extracted with CH$_2$Cl$_2$ (3×200 mL), and the combined organic phases were dried with MgSO$_4$, filtered, and concentrated in vacuo to give 6.2 g (28.44 mmol, 74%) of crude intermediate, S-63 (95% purity according to G.L.C), which was used without further purification.: MS m/e 218.45 (M$^+$, 13.2), 190.4 (13.4), 189.4 (100), 120.25 (19.1), 119.25 (13.6), 106.2 (13.4), 86.30 (10.9), 70.15 (19.0).

EXAMPLE 68

S-(−)-3-(3-Bromophenyl)-N-n-propylpiperidine (S-(−)-64) (Scheme 4)

To a solution of the amine hydrochloride S-63 (16.28 g, 55.96 mmol) in 100 mL of 48% aqueous HBr at 0° C.C was added dropwise with stirring a solution of NaNO$_2$ (4.2 g, 60.96 mmol) in 4 mL H$_2$O. The reaction mixture was stirred for 1 h at 0° C.C under Ar-atmosphere. Cuprous bromide (8.2 g, 57.16 mmol) dissolved in 20 mL of 48% HBr was added, and the solution was heated at 80° C.C for 40 min. After cooling, 100 mL of water was added and the reaction mixture was made alkaline with concentrated ammonia. The aqeous solution was extracted with CH$_2$Cl$_2$ (3×60 mL). The combined organic phases were dried (MgSO$_4$), filtered, and the solvent was evaporated in vacuo to give 13.6 g (85%) of crude S-64. The residue was purified by flash chromatography using CH$_2$Cl$_2$/MeOH (9/1) as eluent, affording pure S-64 (9.05 g, 57.3%). The amine was converted to the hydrochloride salt with ethereal HCl. The S-64×HCl was recrystallized in ethanol:isopropylether: m.p. 209°–11° C. (HCl); MS m/e 283.05 (M$^+$+1, 2.8), 282.05 (M$^+$, 1.9), 281.05 (M$^+$−1, 3.4), 254.95 (12.1), 253.95 (94.2), 251.95 (100), 129.95 (30.8), 128.95 (31.7), 115.95 (20.6), 114.95 (23.7);)a)$_D^{20}$ −7.9° C. (c=1.0, MeOH); Analysis calc'd for C$_{14}$H$_{21}$NBrCl: C, 52.77; H, 6.64; N, 4.40; found: C, 52.9; H, 6.8; N, 4.6.

EXAMPLE 69

S-3-(3-Thiomethylphenyl)-N-n-propylpiperidine (S-65) (Scheme 4)

To a solution of S-(−)-64 (1.0 g, 3.56 mmol) in dry diethylether (20 mL) at −78° C.C were added a solution of s-butyllithium in hexane (1.4M, 3.56 mL, 4.98 mmol). The solution was stirred at −78° C.C for 15 min., allowed to warm to 0° C.C, stirred for additional 30 min. at 0° C.C, brought to −78° C.C, and then was treated with dimethyl disulfide (502 mg, 5.34 mmol). The reaction mixture was allowed to warm to room temperature and stirred for 1 h. The reaction mixture was then diluted with 10% Na$_2$CO$_3$ and the phases were separated. The aqueous phase was extracted with diethylether (3×30 mL) and the combined organic phases were washed with brine, dried (MgSO$_4$), filtered, and concentrated in vacuo to give 980 mg (110%) of crude S-65. The residue was purified by flash chromatography using CH$_2$Cl$_2$/MeOH (12/1) as eluent, affording pure S-65 (560 mg, 63%). The amine was converted to the hydrochloride salt with ethereal HCl. The S-65×HCl was recrystallized in ethanol:isopropylether: MS m/e 249.25 (M$^+$, 7.9), 221.15 (15.3), 220.15 (100), 150.15 (5.2), 129.15 (7.3), 115.05 (6.9).

EXAMPLE 70

S-3-(3-Methylsulfonylphenyl)-N-n-propylpiperidine (S-66) (Scheme 4)

To a solution of S-65 (560 mg, 2.25 mmol) in trifluoroacetic acid (5 mL) was added a solution of m-chloroperbenzoic acid (970 mg, 3.62 mmol) in trifluoro-acetic acid (3 mL). The solution was stirred at room temperature for 3 h and poured into ice water. The resulting mixture was made alkaline with 15% NaOH, and extracted with CH$_2$Cl$_2$ (3×25 mL). The combined organic phases were dried (MgSO$_4$), filtered, and concentrated in vacuo. The oily residue was purified by flash chromatography using CH$_2$Cl$_2$/MeOH (9/1) as eluent, affording pure S-66 (537 mg, 85%). The amine was converted into the fumarate salt and recrystallized in ethanol:isopropyl ether: m.p. 105°–08° C. (fumarate); MS m/e calc'd for NO$_2$SC$_{15}$H$_{23}$: 281.145, found 281.143; 281.25 (M$^+$, 2.9), 253.15 (16.1), 252.15 (100), 129.15 (9.6), 70.15 (6.4).

EXAMPLE 71

S-3-(3-Trifluoromethylsulfonylphenyl)-N-n-propylpiperidine (S-67) (Scheme 4)

To a solution of S-64 (1.0 g, 3.56 mmol) in dry diethylether (20 mL) at −78° C.C was added a solution of s-butyllithium in hexane (1.4M, 3.56 mL, 4.98 mmol). The solution was stirred at −78° C.C for 15 min., allowed to warm to 0° C.C. After an additional 30 min. at 0° C.C. the mixture was brought to −78° C.C. and treated with tri-fluoromethanesulfonic anhydride (1.1 g, 3.91 mmol). The reaction mixture was allowed to warm to room temperature and stirred for 1 h. The reaction mixture was then diluted with 10% Na$_2$CO$_3$ and the phases were separated. The aqueous phase was extracted with diethylether (3×30 mL) and the combined organic phases were washed with brine, dried (MgSO$_4$), filtered, and concentrated in vacuo.; MS m/e calc'd for F$_3$NO$_2$SC$_{15}$H$_{20}$:335.117, found 335.099; 335.1 (M$^+$, 5.0), 202.25 (10.7), 144.15 (17.3), 129.15 (18.2), 117.15 (35.9), 115.15 (21.1), 91.15 (25.9), 72.15 (100).

EXAMPLE 72

S-3-(3-Aminosulfonylphenyl)-N-n-propylpiperidine (S-68) (Scheme 4)

To a solution of S-64 (700 mg, 2.49 mmol) in dry THF (20 mL) at −78° C.C. was added a solution of s-butyllithium in hexane (1.4M, 2.66 mL, 3.73 mmol). The solution was stirred at −78° C.C. for 15 min. and allowed to warm to 0° C.C. After an additional 30 min. at 0° C.C. the solution was brought to −78° C.C., at which time dry sulfur dioxide gas was passed into the reaction vessel via a needle positioned just above the surface of the solution for 20 min. to give a copious precipitate. The reaction mixture was allowed to warm to room temperature and stirred for 1 h under SO$_2$ (g). The reaction mixture was then concentrated in vacuo and pretreated with CH$_2$Cl$_2$ (25 mL). The suspension was cooled to 0° C.C. and SO$_2$Cl$_2$ (3 mL) was added dropwise. After 2 h the mixture was concentrated in vacuo to remove excess of SOCl$_2$. The oily residue was dissolved in CH$_2$Cl$_2$ (35 mL) and cooled to 0° C.C. Ammonia gas was bubbled through the solution for 20 min. The suspension was filtered through a pad of celite and washed several times with CH$_2$Cl$_2$. The organic phase was washed with brine, dried (MgSO$_4$), filtered, and concentrated in vacuo.: MS m/e calc'd for N$_2$O$_2$SC$_{14}$H$_{22}$: 282.140, found 282.139; 282.25 (M$^+$, 2.9), 254.15 (13.5), 253.15 (100), 129.15 (9.9), 128.15 (7.3), 115.15 (6.9).

EXAMPLE 73

5-(2,6-Dichlorophenyl)-2-piperidone (Intermediate, Racemic-69)

A solution of diisopropylamine (19.2 mL, 0.135 mol) in THF (75 mL) was added dropwise at room temperature to n-BuLi in hexane (67.5 mL, 0.135 mol) under argon atmosphere. The mixture was stirred for 0.5 h and then brought to −78° C.C. A solution of 2,6-dichlorophenyl acetonitrile (25 g, 0.135 mol) in THF (50 mL) was added dropwise while the reaction mixture was maintained at −78° C.C. The resulting mixture was stirred for 1 h, whereafter a solution of ethyl-3-bromoproionate (17.2 mL, 0.135 mol) in THF (50 mL) was added dropwise. The resulting mixture was stirred for 1 h, and then allowed to reach room temperature. After an additional 1 h at 25° C.C., the mixture was quenched with 10% aqueous hydrochloride solution. The phases were separated and the aqueous phase was extracted with diethyl ether (3×75 mL). The combined organic phases were dried ($MgSO_4$), filtered, and concen-trated in vacuo affording ethyl-4-cyano-4-(2,6-dichlorophenyl)-butanoate (37 g) as an oil. A solution of the butanoate (3.53 g, 15 mmol) in HCl-saturated ethanol (100 mL) was hydrogenated at 50 psi over $PtO_2$ (0.9 g) in a Parr apparatus. Removal of the catalyst by filtration, followed by evaporation of the EtOH, yielded an oily residue. The oil was taken up in 15% NaOH and was extracted with diethylether (3×30 mL), dried, filtered, and concentrated in vacuo. The oily residue was purified by flash chromatography using $CH_2Cl_2$/MeOH (19/1) as eluent, affording pure racemic-69 (0.9 g, 85%): MS m/e 244.95 ($M^++1$, 15.1), 243.95 ($M^+$, 3.5), 242.95 ($M^+-1$, 24.1), 208.00 (19.3), 179.00 (29.3), 173.9 (61.3), 171.9 (100), 137.00 (31.6), 115.00 (20.5)

EXAMPLE 74

3-(2,6-Dichlorophenyl)-piperidine (Racemic-70)

A solution of racemic-69 (0.35 g, 1.43 mmol) in 1,2.dichloroethane (10 mL) was added in one portion to a solution of $QBH_4$ (1.75 g, 7.6 mmol) and activated molecular sieves (4Å) in $CH_2Cl_2$ (10 mL). The mixture was refluxed and after 3 h GC revealed complete absence of starting racemic-69. The reaction mixture was cooled to room temperature and concentrated in vacuo. The residue was redissolved in toluene (30 mL), and the solution was washed with water (3×30 mL), dried ($MgSO_4$), filtered, and the solvent was evaporated in vacuo to yield 0.314 g of crude racemic-70. The oily residue was purified by flash chromatography using petroleum ether/etylacetate (9/1) as eluent, affording pure racemic-70 (230 mg, 73%).: MS m/e 230.95 ($M^++1$, 16.5), 230.05 ($M^+$, 7.8), 229.05 ($M^+-1$, 26.0), 194.05 (33.9), 171.95 (25.0), 136.95 (30.8), 101.05 (23.4), 70.05 (21.4), 57.05 (100), 56.05 (61.3)

EXAMPLE 75

3-(2,6-Dichlorophenyl)-N-n-propylpiperidine (Racemic-71) (Scheme 3)

This compound was prepared as described for S-37 from racemic-70 (220 mg, 0.95 mmol) and n-propylbromide (128 mg, 1.04 mmol). Purification of the crude reaction mixture by flash chromatography (petroleum ether/ether, 12/1 by volume) afforded 177 mg (68%) of pure racemic-71 as an oil: MS m/e 273.1 ($M^++1$, 1.4), 271.10 ($M^+-1$, 2.4), 244.00 (58.8), 242.00 (100), 160.9 (9.5), 158.9 (15.4), exact mass calcd for $C_{14}H_{19}NCl_2$ 271.0894, found 271.0860.

EXAMPLE 76

5-Nitro-(3-methoxyphenyl)-2-pentanone. (Intermediate, Racemic-72) (Scheme 5)

A mixture of 3-methoxynitrostyrene (6.96 g, 39 mmol) and ethyl-3-pyrrolidino-2-butenoate (7.10 g, 39 mmol) was refluxed in ethanol (100 mL) for 4.0 h. The solvent was then removed and the residue refluxed in 10% HCl (50 mL) for 2.0 h. After cooling to ambient temperature the reaction mixture was extracted with ethyl ether (3×25 mL). The extract was dried ($MgSO_4$) and the solvent removed to yield 9.40 g of crude material as an oil. This was distilled twice using a Kugelrohr oven (225° C. C/0.4mm Hg) yielding 4.83 g of product. This was further purified by flash chromatography (n-hexane/ethyl acetate 1/1), yielding 3.25 g (35%) of a colorless oil.: MS (EI) m/e 237.15 ($M^+$, 22), 190.05 (100), 175.05 (32), 149.05 (35), 148.05 (37), 134.05 (36), 115 (10, 20), 91.00 (28), 77.00 (21).

EXAMPLE 77

Cis and trans-2-Methyl-4-(3-methoxyphenyl)-pyrrolidine. (Racemic-73) (Scheme 5)

5-Nitro-(3-methoxyphenyl)-2-pentanone (500 mg, 2.10 mmol) was dissolved in absolute ethanol (50 mL). Platinum oxide (100 mg) was added to the solution, and hydrogenated in an Parr apparatus at 50 psi for one hour. The solution was then filtered through a celite pad to remove the catalyst. Evaporation of the solvent gave 390 mg of a colorless oil (97%). The ratio of cis and trans isomers was 91:9.: MS (EI) m/e 191.25 (19, $M^+$), 190.25 (10), 176.25 (30), 57.15 (100), 56.15 (15).

EXAMPLE 78

Cis-2-Methyl-4-(3-methoxyphenyl)-N-benzylpyrrolidine. (Racemic-74) Scheme 5)

To a stirred solution of 2-methyl-4-(3-methoxyphenyl)-pyrrolidine (cis and trans 91:9, 390 mg, 2.04 mmol) in 1,2-dichloroethane was added benzaldehyde (250 mg, 2.36 mmol), sodium triacetoxyborohydride (640 mg, 3.00 mmol) and acetic acid (0.20 mL). The mixture was stirred at room temperature for 4 hours. The solvent was removed and the residue was dissolved in 10% hydrochloric acid (20 mL). The acidic solution was washed with diethyl ether (2×20 mL). The amine was then liberated by the addition of 50% sodium hydroxide (20 mL). The product was extracted with diethyl ether (3×20 mL). Drying ($MgSO_4$) and evaporation of the solvent afforded 450 mg of a slightly red oil. The pure cis-74 was then obtained by HPLC on a $SiO_2$ column (n-hexane/EtOAc/EtOH 90/8/2), yielding 270 mg (52%).; MS (EI) m/e calc'd for $C_{19}H_{23}NO$: 281.178, found 281.178; 281.35 (11, $M^+$), 267.25 (19), 266.25 (94), 147.15 (14), 146.25 (11), 91.15 (100).

EXAMPLE 79

Cis-and-trans-2-Methyl-4-(3-methoxyphenyl)-N-propionyl-pyrrolidine. (Racemic-75) (Scheme 5)

To a stirred solution of 2-methyl-4-(3-methoxyphenyl)-pyrrolidine (cis and trans: 91:9, 300 mg, 1.57 mmol) in dichloromethane (10 mL) was added triethyl amine (0.50 mL, 3.60 mmol) and propionyl chloride (210 mg, 2.27 mmol). The mixture was stirred at room temperature for 30 min followed by addition of 10% sodium carbonate solution (10 mL) was added an stirring continued for an additional 30 min. The dichloromethane layer was separated, washed with water (10 mL), 10% hydrochloric acid (10 mL) and dried ($MgSO_4$). Evaporation of the solvent afforded 380 mg of crude material which was purified by flash chromatography (dichloromethane/methanol 19/1). A yield of 340 mg (88%) of product was obtained as a colorless oil. The ratio of cis and trans isomers was 86:14 according to GC analysis. A small sample (20 mg) of the cis isomer was isolated by HPLC on a $SiO_2$ column (hexane/EtOAc/EtOH 91/8/1).: MS (EI) m/e cis isomer: 247.15 (33, $M^+$), 190.15 (12), 176.05 (100), 149.05 (11), 134.05 (17), 113.05 (19), 100.05 (12), 90.95 (10) trans isomer: 247.15 (34, $M^+$), 190.15 (13), 176.05 (100), 149.05 (11), 134.05 (18), 113.05 (19), 100.05 (14), 90.95 (10).

EXAMPLE 80

Cis-and-trans-2-Methyl-4-(3-methoxyphenyl)-N-n-propyl-pyrrolidine. (Racemic-76) (Scheme 5)

To a stirred solution of 2-methyl-4-(3-methoxyphenyl)-N-propionyl-pyrrolidine (cis and trans isomers 86: 14, 320 mg, 1.30 mmol) in 1,2-dichloro-ethane (20 mL) was added tetrabutylammonium borohydride (660 mg, 2.57 mmol). The mixture was heated at reflux temperature for 2.5 hours, when an additional portion of the borohydride (330 mg, 1.28 mmol) was added. Stirring and heating was then continued for 2.5 hours. The solvent was removed and the residue was dissolved in 10% hydrochloric acid (20 mL). The acidic solution was heated at reflux for 1 hour and then washed with diethyl ether, made alkaline with 50% sodium hydroxide (20 mL) and the liberated amine extracted with ethyl acetate (3×20 mL). Drying ($MgSO_4$) and removal of the solvent yielded 280 mg of crude product. Flash chromatography (dichloromethane/methanol 19/1) afforded 270 mg (89%) of colorless oil. The ratio of cis and trans isomers was 85:15. A pure sample (28 mg) of the cis isomer was obtained by HPLC on a $SiO_2$ column (n-hexane/EtOAc/MeOH 91/8/1).:MS (EI) m/e cis isomer: calc'd for $C_{15}H_{23}NO$: 233.178, found 233.178; 233.25 (10, $M^+$), 218.25 (50), 205.25 (15), 204.25 (100), 121.15 (10), 102.15 (8), 91.15 (9), 84.15 (17) trans isomer: 233.25 (11, $M^+$), 218.25 (57), 205.25 (14), 204.25 (100), 121.12 (9), 102.15 (5), 91.15 (8), 84.15 (13).

EXAMPLE 81

Cis -2-Methyl-4-(3-hydroxyphenyl)-N-n-propylpyrrolidine. (Racemic-cis-77)

2-Methyl-4-(3-methoxyphenyl)-N-n-propylpyrrolidine (cis and trans mixture 85: 15, 920 mg, 3.95 mmol) was dissolved in 47% hydrobromic acid (20 mL) and heated at reflux temperature for 1.5 hours. The mixture was made alkaline by the addition of 10% sodium carbonate (75 mL) and the product extracted with diethyl ether and ethyl acetate (1:1,3×20 mL). Drying ($MgSO_4$) afforded 840 mg of the crude product as a white solid. Chromatography on a $SiO_2$ HPLC column yielded 601 mg of the title compound.: m.p. 123°–24° C.; MS (EI) m/e calc'd for $C_{14}H_{21}NO$: 219.162, found 219.163; 219.15 (10, $M^+$), 204.05 (47), 191.05 (14), 190.05 (100), 161.05 (6), 133.05 (6), 106.95 (8), 90.95 (6), 84.05 (12).

EXAMPLE 82

Trans-2-Methyl-4-(3-hydroxyphenyl)-N-n-propylpyrrolidine. (Racemic-trans-77) (Scheme 5)

Trans 2-Methyl-4-(3-hydroxyphenyl)-N-n-propylpyrrolidine was prepared as described for compound (cis-77). The yield of the title compound after chromato-graphy was 72 mg (55%) of a colorless oil.: MS (EI) m/e calc'd for $C_{14}H_{21}NO$: 219.162, found 219.163; 219.15 (10, $M^+$), 204.15 (48), 191.05 (13), 190.05 (100), 161.05 (6), 133.05 (5), 106.95 (7), 90.95 (4), 84.05 (8).

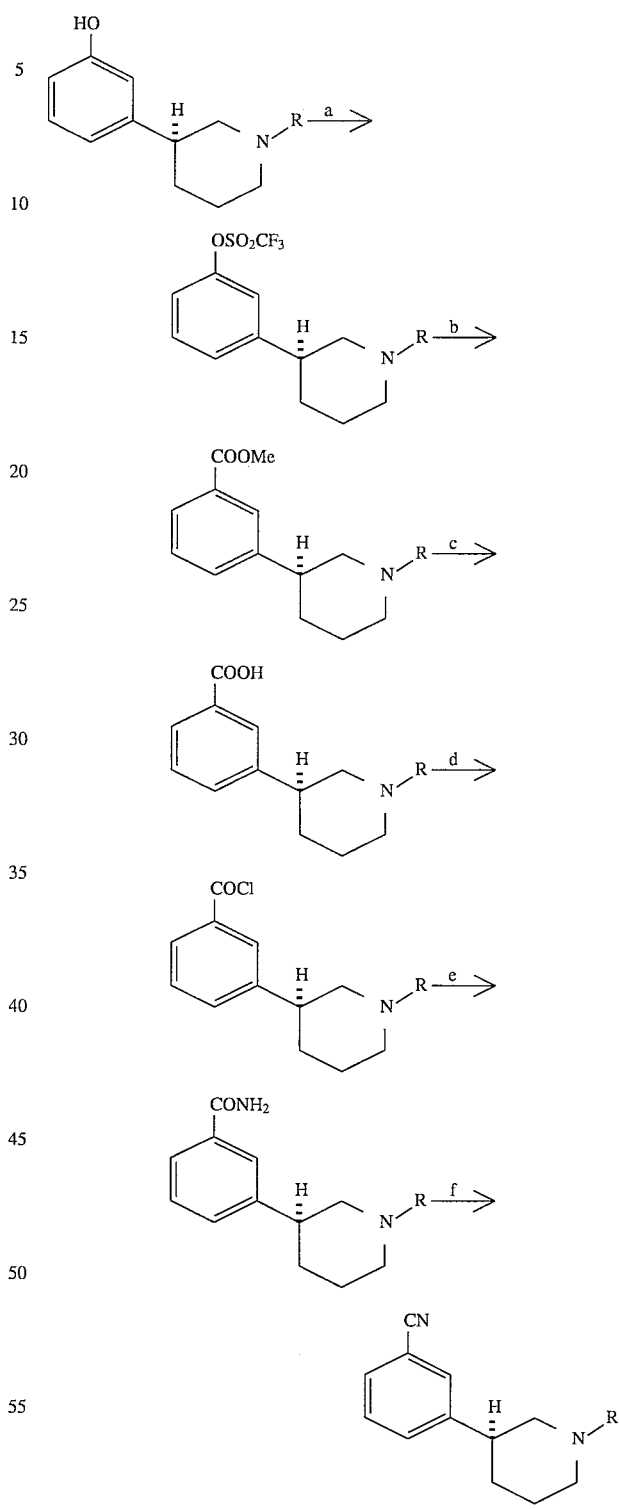

Scheme 1

Reagents: a) $(CF_3SO_2)_2O$ b) $Pd(OAc)_2$ and CO(g) c) 10% NaOH d) $SOCl_2$ e) $NH_3$ f) $POCl_3$

Scheme 2
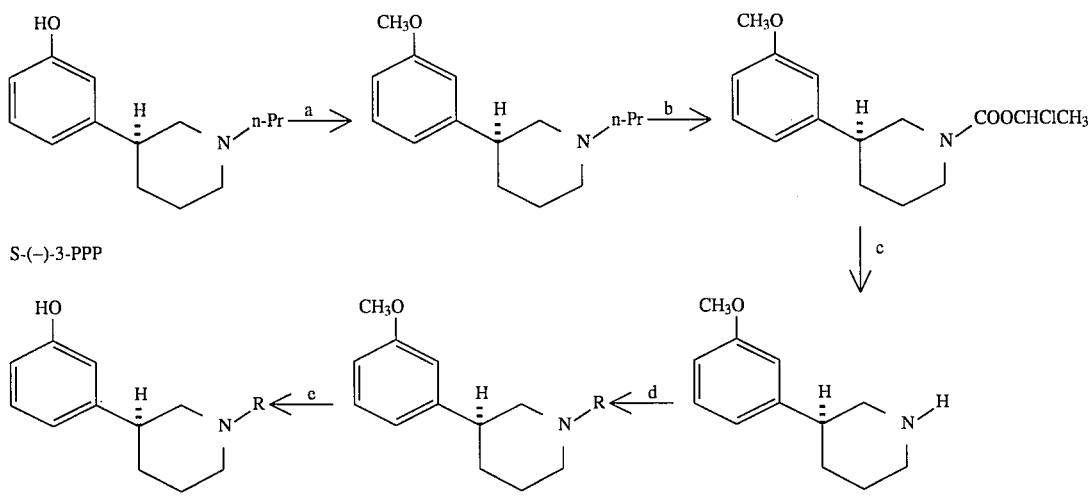
Reagents: a) NaOH, (CH₃)₂SO₄ b) CH₃CHClOCOCl c) MeOH
d) R₁CHO (where R = R₁CH₂) and NaBH₃CN e) 48% HBr
Scheme 3
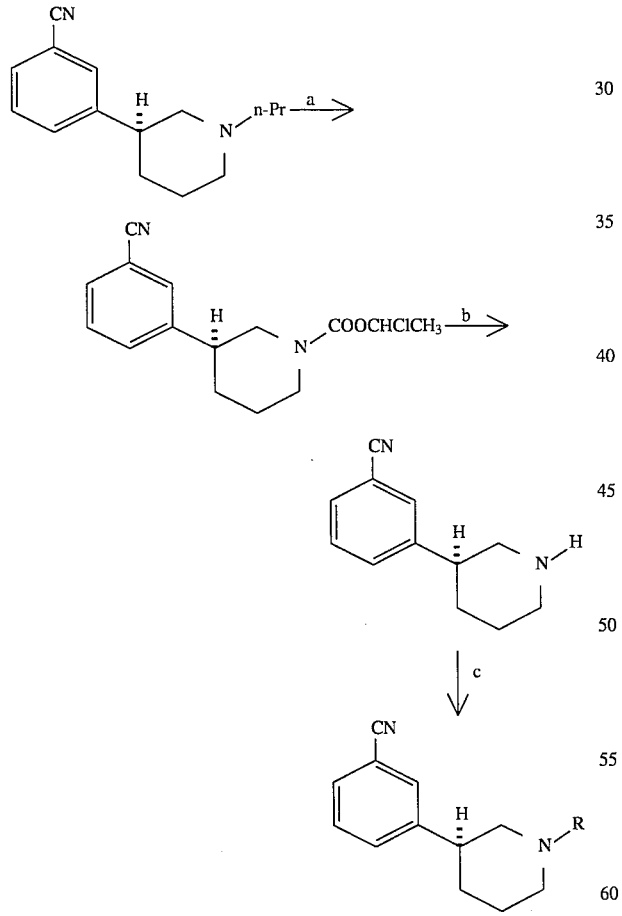
Reagents: a) CH₃CHClOCOCl b) MeOH c) K₂CO₃, RX

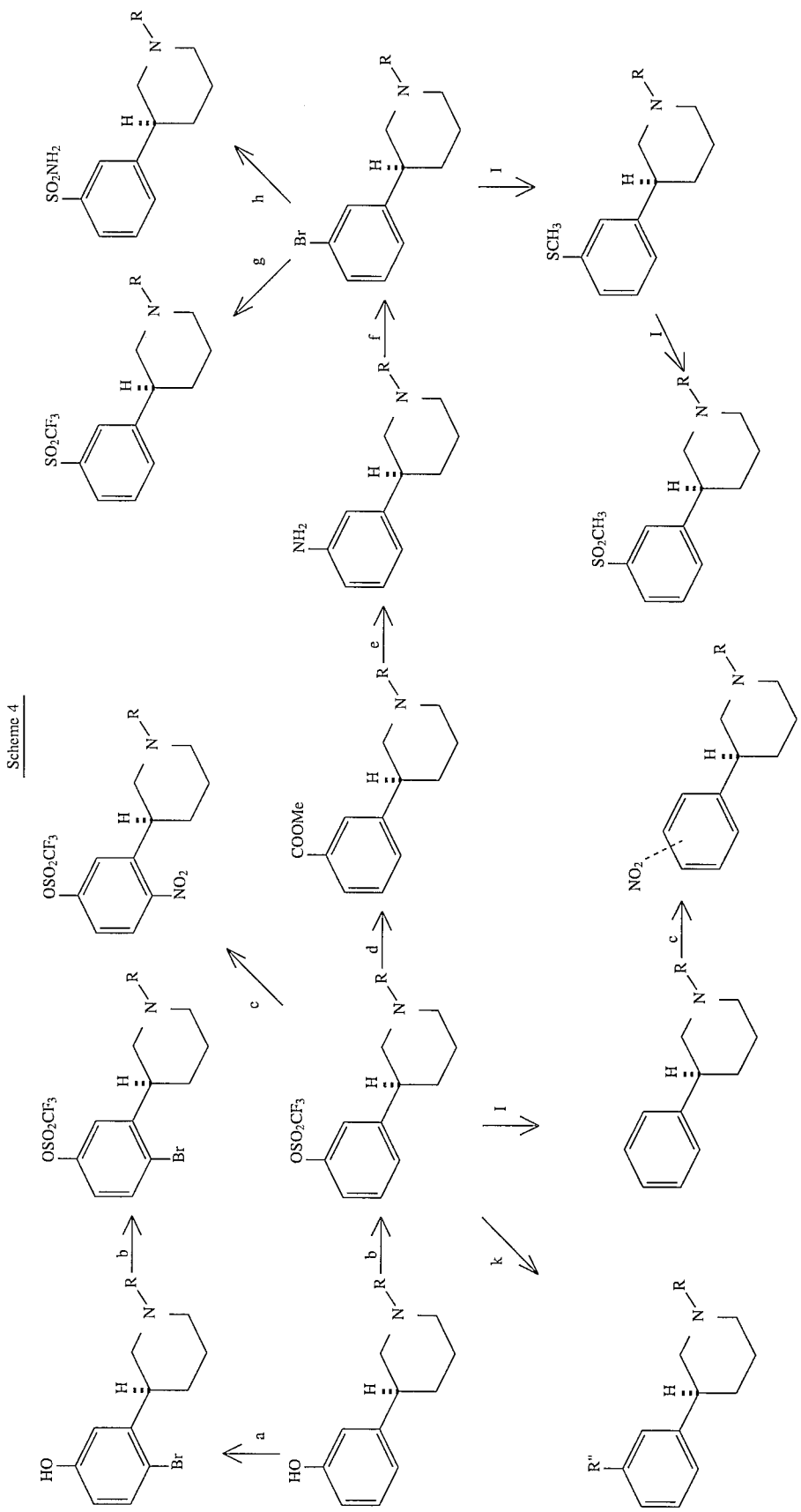
Reagents: a) Pyridinium bromide perbromide b) (CF$_3$SO$_2$)$_2$O c) HNO$_3$/H$_2$SO$_4$ d) Pd(OAc)$_2$, CO(g) e) H$_2$SO$_4$, NaN$_3$
f) CuBr, NaNO$_2$ g) BuLi, (CF$_3$SO$_2$)$_2$O h) BuLi, SO$_2$(g), NH$_3$(g) f) BuLi, CH$_3$SSCH$_3$) MCPBA, CF$_3$COOH
k) "Pd*", R$_3$SnR") Pd(OAc)$_2$, HCO$_2$H

Scheme 5

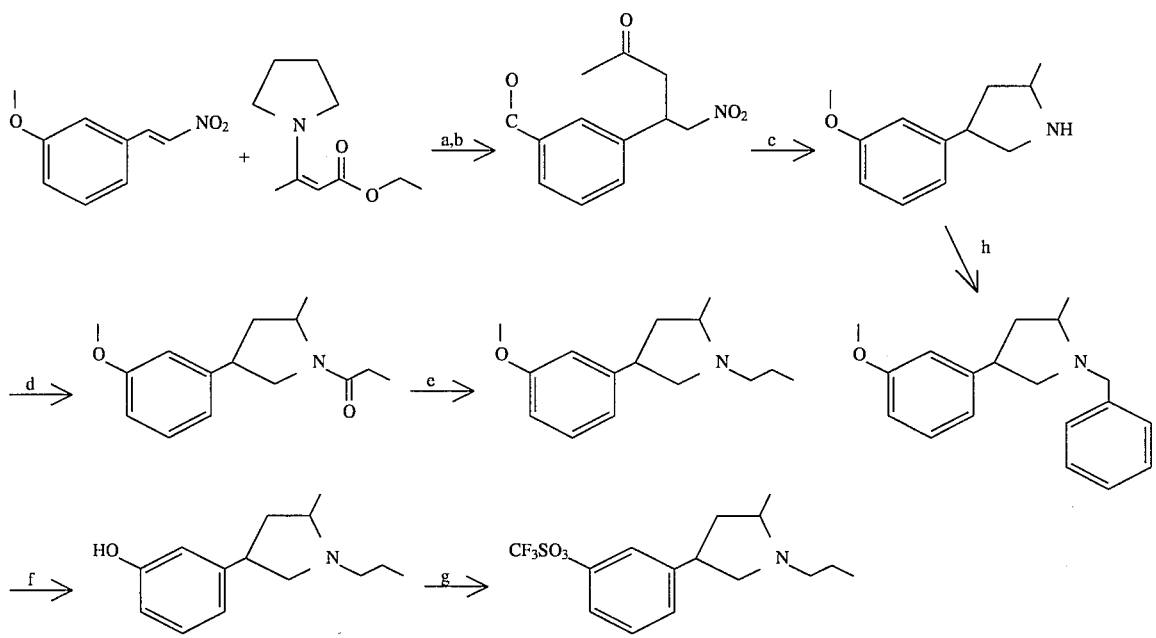

Reagents: a) EtOH, Δ b) HCl, Δ c) EtOH, Pt/H₂ d) TEA, propionylchloride, CH₂Cl₂ e) QBH₄, DCE
f) 47% HBr g) triflic anhydride, TEA h) benzaldehyde, Na(AcO)₃BH, DCE

What is claimed:

1. A compound of Formula I

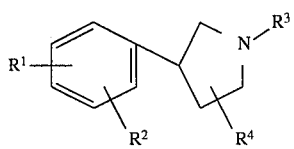

or a pharmaceutically acceptable salt thereof, $R^1$ and $R^2$ are independently H (provided that not more than one is H), OH (provided that not more than one is OH), CN, CH$_2$CN, OSO$_2$CH$_3$, OSO$_2$CF$_3$, SSO$_2$CF$_3$, COR, SO$_x$CH$_3$ (where x is 0–2), SO$_2$CF$_3$, O(CH$_2$)$_x$CF$_3$, SO$_2$N(R)$_2$, CH=NOR, COCOOR, COCOON(R)$_2$, C$_{3-8}$ cycloalkyl, NRSO$_2$CF$_3$, phenyl at position 2, 3 or 4, thienyl, furyl, pyrrolyl, oxazolyl, thiazolyl, N-pyrrolinyl, triazolyl, tetrazolyl or pyridinyl;

$R^3$ is hydrogen, CF$_3$, CH$_2$CF$_3$, C$_1$–C$_8$ alkyl, C$_3$–C$_8$ cycloalkyl, C$_4$–C$_9$ cycloalkyl-methyl, C$_2$–C$_8$ alkenyl, C$_2$–C$_8$ alkynyl, 3,3,3-trifluoropropyl, 4,4,4-trifluorobutyl, —(CH$_2$)$_m$—R$^5$ (where m is 1–8), CH$_2$SCH$_3$, or C$_4$–C$_8$ alkylene bonded to the N-atom and one of the adjacent carbon atoms whereby a heterocyclic structure is formed;

$R^4$ and R are independently selected from hydrogen, CF$_3$, CH$_2$CF$_3$, C$_1$–C$_8$ alkyl, C$_3$–C$_8$ cycloalkyl, C$_4$–C$_9$ cycloalkyl-methyl, C$_2$–C$_8$ alkenyl, C$_2$–C$_8$ alkynyl, 3,3,3-trifluoropropyl, 4,4,4-trifluorobutyl or —(CH$_2$)$_m$—R$^5$ where m is 1–8;

$R^5$ is phenyl, phenyl substituted with CN, CF$_3$, CH$_2$CF$_3$, C$_1$–C$_8$ alkyl, C$_3$–C$_8$ cycloalkyl, C$_4$–C$_9$ cycloalkyl-methyl, C$_2$–C$_8$ alkenyl or C$_2$–C$_8$ alkynyl substituent, 2-thiophenyl, 3-thiophenyl, —NR$^6$CONR$^6$R$^7$ or —CONR$^6$R$^7$; and $R^6$ and $R^7$ are independently hydrogen, C$_1$–C$_8$ alkyl, C$_3$–C$_8$ cycloalkyl, C$_4$–C$_9$ cycloalkylmethyl, C$_2$–C$_8$ alkenyl or C$_2$–C$_8$ alkynyl.

2. The compound of claim 1, which is either a pure R or S enantiomer.

3. The compound of claim 1, wherein $R^1$ is CN, OSO$_2$CF$_3$, or SO$_2$CH$_3$.

4. The compound of claim 3, wherein $R^2$ is H and $R^3$ is C$_{1-8}$ alkyl.

5. The compound of claim 4, wherein $R^2$ is H and $R^3$ is n-propyl.

6. The compound of claim 5, wherein $R^4$ is hydrogen.

7. The compound of claim 1, wherein $R^1$ is 3-OH, $R^2$ is H, $R^3$ is n-propyl and $R^4$ is C$_{2-8}$ alkyl.

8. A method for treating depression associated with dopamine receptor activity comprising: administering to a patient in need thereof a pharmaceutically effective amount of a compound of claim 1.

9. The method of claim 8, wherein the compound is administered to a patient in an amount of 50–500 mg/70 kg orally or 0.5 to 50 mg/70 kg parenterally.

* * * * *